US007317078B2

(12) United States Patent
Crofts et al.

(10) Patent No.: US 7,317,078 B2
(45) Date of Patent: Jan. 8, 2008

(54) ISOFORMS OF THE HUMAN VITAMIN D RECEPTOR

(75) Inventors: Linda Anne Crofts, Erskineville (AU); Manuela S. Hancock, Collingwood (AU); Nigel A. Morrison, Sorrento (AU); John A. Eisman, Paddington (AU)

(73) Assignee: Garvan Institute of Medical Research, Darlinghurst, New South Wales (AU)

( * ) Notice: Subject to any disclaimer, the term of this patent is extended or adjusted under 35 U.S.C. 154(b) by 146 days.

(21) Appl. No.: 11/156,272

(22) Filed: Jun. 17, 2005

(65) Prior Publication Data

US 2006/0030002 A1 Feb. 9, 2006

Related U.S. Application Data

(62) Division of application No. 09/509,482, filed as application No. PCT/AU98/00817 on Sep. 29, 1998, now Pat. No. 6,998,473.

(30) Foreign Application Priority Data

Sep. 29, 1997 (AU) .................................... PO9500

(51) Int. Cl.
*C07K 14/705* (2006.01)

(52) U.S. Cl. ...................................... 530/300; 530/350

(58) Field of Classification Search ..................... None
See application file for complete search history.

(56) References Cited

OTHER PUBLICATIONS

Baker, A.R. et al. "Cloning and expression of full-length cDNA encoding human vitamin D receptor", Proc. Nat. Acad. Sci. USA., 85:3294-3298, 1988.

Goto, H. et al., A single receptor identical with that from intestine/T47D cells mediates the action of 1,25-dihydroxyvitamin D-3 in HL-60 cellsBiochim Biophys Acta., 1132:103-108, 1992.

Miyamoto, K. et al., "Structural organization of the human vitamin D receptor chromosomal gene and its promoter", Mol. Endocrin. 11(8): 1165-1179, 1997.

Crofts, L.A. et al., "Multiple promoters direct the tissue-specific expression of novel N-terminal variant human vitamin D receptor gene transcripts", Proc. Nat. Acad. Sci. USA, 95:10529-10534, 1998.

Whitehead, R. H. et al., "A New Colon Carcinoma Cell Line (LIM1863) That Grows as Organoids With Spontaneous Differentiation into Crypt-Like Structures in Vitro", Cancer Research 47; 2683-2689 (May 15, 1987).

Slater, M. et al., "Modulation of Growth factor Incorporation into ECM of Human Osteoblast-Like Cells in Vitro by 17β-estradiol", Cancer Research 47; 2683-2689 (May 15, 1987).

Saijo, T. et al., "A Unique Mutation in the Vitamin D receptor Gene in Three Japanese Patients with Vitamin-D dependent Rickets Type II: Utility of Single-Strand Conformation Polymorphism Analysis for Heterozygous Carrier Detection", Am. J. Hum. Genet. 49: 668-673 (1991).

Lu, Z. et al., "Cloning and Origin of the Two forms of Chicken Vitamin D Receptor", Archives of Biochemistry and Biophysics vol. 339, No. 1; 99-106 (1997).

Ebihara, K. et al., "*Intron Retention Generates A Novel Isoforms of the Murine Vitamin D Receptor That Acts in a Dominant Negative Way on the Vitamin D Signaling Pathway*", Molecular and Cellular Biology: 3393-3400 (1996).

MacDonald et al. Baculovirus-mediated expression of the human vitamine D receptor, Oct. 5, 1991, J. Biol. Chem. 266(28): 18808-18813.

Haussler M. R. et al., "The vitamin D hormone and its nuclear receptor: molecular actions and disease states", Journal of Endocrinology, Bristol, GB, (1997), vol. 154, pp. s57-s73.

Jurutka, et al., "Human D receptor phosphorylation by casein kinase II at ser-208 potentiates transcriptional activation", Proc. Natl. Acad. Sci. USA, (1996), vol. 93, pp. 3519-3524.

Sunn KL, et al., "Novel N-terminal variant of human VDR", Molecular Endocrinology 15 (9): 1599-1609, (Sep. 2001).

*Primary Examiner*—John Ulm
(74) *Attorney, Agent, or Firm*—Carol L. Francis; Bozicevic, Field & Francis LLP

(57) ABSTRACT

The invention provides isolated polynucleotide molecules which encode novel isoforms of the human Vitamin D receptor (hVDR) or variant transcripts for hVDR. These isolated polynucleotide molecules may be utilized in, for example, methods of screening compounds for VDR agonist and/or antagonist activities.

9 Claims, 21 Drawing Sheets

FIG. 4

A. 5'...atcccttaag GGCTCCTGAACCTAGCCCAGCTGGACGGAG
AAATGGACTCTAGCCTCCTCTGATAGCCTCATGCCAGGCCC
CGTGCACATTGCTTTGCTTGCCTCCCTCAATCCTCATAGCT
TCTCTTTGGGgtaagtacag...3' (SEQ ID NO: 13)

B. 5'...TGCGACCTTGGCGGTGAGCCTGGGGACAGGGGTGAGGC
CAGAGACGGACGGACGCAGGGGCCCGGCCCAAGGCGAGGG
AGAACAGCGGCACTAAGGCAGAAAGGAAGAGGGCGGTGTG
TTCACCCGCAGCCCAATCCATCACTCAGCAACTCCTAGAC
GCTGGTAGAAAGTTCCTCCGAGGAGCCTGCCATCCAGTCGT
GCGTGCAG...3' (SEQ ID NO: 5)

C. 5'...tgtttttag AGGCAGCATGAAACAGTGGGATGTGCAGAG
AGAAGATCTGGGTCCAGTAGCTCTGACACTCCTCAGCTGT
AGAAACCTTGACAACTCTGCACATCAGTTGTACAATGGAA
CGGTATTTTTTACTCTTCATGTCTGAAAAGGCTATGATAA
AGATCAAgtaagatatt...3' (SEQ ID NO: 6)

D. 5'...GTTTCCTTCTTCTGTCGGGGCGCCTTGGCATGGAGTGG
AGGAATAAGAAAAGGAGCGATTGGCTGTCGATGGTGCTCA
GAACTGCTGGAGTGGAGGgtgtgtaacc...3' (SEQ ID NO: 22)

FIG. 5A

Transcript 6
(Sequence Range: 1 to 1463)

```
        10         20         30         40         50
     *    *     *    *     *    *     *    *     *    *
GTTTCCTTCT TCTGTCGGGG CGCCTTGGCA TGGAGTGGAG GAATAAGAAA
CAAAGGAAGA AGACAGCCCC GCGGAACCGT ACCTCACCTC CTTATTCTTT
                                MetGluTrpArg AsnLysLys>

        60         70         80         90        100
     *    *     *    *     *    *     *    *     *    *
AGGAGCGATT GGCTGTCGAT GGTGCTCAGA ACTGCTGGAG TGGAGGAAGC
TCCTCGCTAA CCGACAGCTA CCACGAGTCT TGACGACCTC ACCTCCTTCG
ArgSerAsp TrpLeuSerMet ValLeuArg ThrAlaGly ValGluGluAla>

       110        120        130        140        150
     *    *     *    *     *    *     *    *     *    *
CTTTGGGTCT GAAGTGTCTG TGAGACCTCA CAGAAGAGCA CCCCTGGGCT
GAAACCCAGA CTTCACAGAC ACTCTGGAGT GTCTTCTCGT GGGGACCCGA
 PheGlySer GluValSer ValArgProHis ArgArgAla ProLeuGly>

       160        170        180        190        200
     *    *     *    *     *    *     *    *     *    *
CCACTTACCT GCCCCCTGCT CCTTCAGGGA TGGAGGCAAT GGCGGCCAGC
GGTGAATGGA CGGGGGACGA GGAAGTCCCT ACCTCCGTTA CCGCCGGTCG
SerThrTyrLeu ProProAla ProSerGly MetGluAlaMet AlaAlaSer>

       210        220        230        240        250
     *    *     *    *     *    *     *    *     *    *
ACTTCCCTGC CTGACCCTGG AGACTTTGAC CGGAACGTGC CCCGGATCTG
TGAAGGGACG GACTGGGACC TCTGAAACTG GCCTTGCACG GGGCCTAGAC
ThrSerLeu ProAspProGly AspPheAsp ArgAsnVal ProArgIleCys>

       260        270        280        290        300
     *    *     *    *     *    *     *    *     *    *
TGGGGTGTGT GGAGACCGAG CCACTGGCTT TCACTTCAAT GCTATGACCT
ACCCCACACA CCTCTGGCTC GGTGACCGAA AGTGAAGTTA CGATACTGGA
 GlyValCys GlyAspArg AlaThrGlyPhe HisPheAsn AlaMetThr>

       310        320        330        340        350
     *    *     *    *     *    *     *    *     *    *
GTGAAGGCTG CAAAGGCTTC TTCAGGCGAA GCATGAAGCG GAAGGCACTA
CACTTCCGAC GTTTCCGAAG AAGTCCGCTT CGTACTTCGC CTTCCGTGAT
CysGluGlyCys LysGlyPhe PheArgArg SerMetLysArg LysAlaLeu>

       360        370        380        390        400
     *    *     *    *     *    *     *    *     *    *
TTCACCTGCC CCTTCAACGG GGACTGCCGC ATCACCAAGG ACAACCGACG
AAGTGGACGG GGAAGTTGCC CCTGACGGCG TAGTGGTTCC TGTTGGCTGC
PheThrCys ProPheAsnGly AspCysArg IleThrLys AspAsnArgArg>
```

FIG. 5B

```
        410         420         430         440         450
         *     *     *     *     *     *     *     *     *     *
CCACTGCCAG GCCTGCCGGC TCAAACGCTG TGTGGACATC GGCATGATGA
GGTGACGGTC CGGACGGCCG AGTTTGCGAC ACACCTGTAG CCGTACTACT
 HisCysGln AlaCysArg LeuLysArgCys ValAspIle GlyMetMet>

        460         470         480         490         500
         *     *     *     *     *     *     *     *     *     *
AGGAGTTCAT TCTGACAGAT GAGGAAGTGC AGAGGAAGCG GGAGATGATC
TCCTCAAGTA AGACTGTCTA CTCCTTCACG TCTCCTTCGC CCTCTACTAG
LysGluPheIle LeuThrAsp GluGluVal GlnArgLysArg GluMetIle>

        510         520         530         540         550
         *     *     *     *     *     *     *     *     *     *
CTGAAGCGGA AGGAGGAGGA GGCCTTGAAG GACAGTCTGC GGCCCAAGCT
GACTTCGCCT TCCTCCTCCT CCGGAACTTC CTGTCAGACG CCGGGTTCGA
 LeuLysArg LysGluGluGlu AlaLeuLys AspSerLeu ArgProLysLeu>

        560         570         580         590         600
         *     *     *     *     *     *     *     *     *     *
GTCTGAGGAG CAGCAGCGCA TCATTGCCAT ACTGCTGGAC GCCCACCATA
CAGACTCCTC GTCGTCGCGT AGTAACGGTA TGACGACCTG CGGGTGGTAT
 SerGluGlu GlnGlnArg IleIleAlaIle LeuLeuAsp AlaHisHis>

        610         620         630         640         650
         *     *     *     *     *     *     *     *     *     *
AGACCTACGA CCCCACCTAC TCCGACTTCT GCCAGTTCCG GCCTCCAGTT
TCTGGATGCT GGGGTGGATG AGGCTGAAGA CGGTCAAGGC CGGAGGTCAA
LysThrTyrAsp ProThrTyr SerAspPhe CysGlnPheArg ProProVal>

        660         670         680         690         700
         *     *     *     *     *     *     *     *     *     *
CGTGTGAATG ATGGTGGAGG GAGCCATCCT TCCAGGCCCA ACTCCAGACA
GCACACTTAC TACCACCTCC CTCGGTAGGA AGGTCCGGGT TGAGGTCTGT
 ArgValAsn AspGlyGlyGly SerHisPro SerArgPro AsnSerArgHis>

        710         720         730         740         750
         *     *     *     *     *     *     *     *     *     *
CACTCCCAGC TTCTCTGGGG ACTCCTCCTC CTCCTGCTCA GATCACTGTA
GTGAGGGTCG AAGAGACCCC TGAGGAGGAG GAGGACGAGT CTAGTGACAT
 ThrProSer PheSerGly AspSerSerSer SerCysSer AspHisCys>

        760         770         780         790         800
         *     *     *     *     *     *     *     *     *     *
TCACCTCTTC AGACATGATG GACTCGTCCA GCTTCTCCAA TCTGGATCTG
AGTGGAGAAG TCTGTACTAC CTGAGCAGGT CGAAGAGGTT AGACCTAGAC
IleThrSerSer AspMetMet AspSerSer SerPheSerAsn LeuAspLeu>

        810         820         830         840         850
         *     *     *     *     *     *     *     *     *     *
AGTGAAGAAG ATTCAGATGA CCCTTCTGTG ACCCTAGAGC TGTCCCAGCT
TCACTTCTTC TAAGTCTACT GGGAAGACAC TGGGATCTCG ACAGGGTCGA
 SerGluGlu AspSerAspAsp ProSerVal ThrLeuGlu LeuSerGlnLeu>
```

FIG. 5C

```
       860       870       880       890       900
         *    *    *    *    *    *    *    *    *    *
CTCCATGCTG CCCCACCTGG CTGACCTGGT CAGTTACAGC ATCCAAAAGG
GAGGTACGAC GGGGTGGACC GACTGGACCA GTCAATGTCG TAGGTTTTCC
 SerMetLeu ProHisLeu AlaAspLeuVal SerTyrSer IleGlnLys>

       910       920       930       940       950
         *    *    *    *    *    *    *    *    *    *
TCATTGGCTT TGCTAAGATG ATACCAGGAT TCAGAGACCT CACCTCTGAG
AGTAACCGAA ACGATTCTAC TATGGTCCTA AGTCTCTGGA GTGGAGACTC
ValIleGlyPhe AlaLysMet IleProGly PheArgAspLeu ThrSerGlu>

       960       970       980       990      1000
         *    *    *    *    *    *    *    *    *    *
GACCAGATCG TACTGCTGAA GTCAAGTGCC ATTGAGGTCA TCATGTTGCG
CTGGTCTAGC ATGACGACTT CAGTTCACGG TAACTCCAGT AGTACAACGC
AspGlnIle ValLeuLeuLys SerSerAla IleGluVal IleMetLeuArg>

      1010      1020      1030      1040      1050
         *    *    *    *    *    *    *    *    *    *
CTCCAATGAG TCCTTCACCA TGGACGACAT GTCCTGGACC TGTGGCAACC
GAGGTTACTC AGGAAGTGGT ACCTGCTGTA CAGGACCTGG ACACCGTTGG
 SerAsnGlu SerPheThr MetAspAspMet SerTrpThr CysGlyAsn>

      1060      1070      1080      1090      1100
         *    *    *    *    *    *    *    *    *    *
AAGACTACAA GTACCGCGTC AGTGACGTGA CCAAAGCCGG ACACAGCCTG
TTCTGATGTT CATGGCGCAG TCACTGCACT GGTTTCGGCC TGTGTCGGAC
GlnAspTyrLys TyrArgVal SerAspVal ThrLysAlaGly HisSerLeu>

      1110      1120      1130      1140      1150
         *    *    *    *    *    *    *    *    *    *
GAGCTGATTG AGCCCCTCAT CAAGTTCCAG GTGGGACTGA AGAAGCTGAA
CTCGACTAAC TCGGGGAGTA GTTCAAGGTC CACCCTGACT TCTTCGACTT
GluLeuIle GluProLeuIle LysPheGln ValGlyLeu LysLysLeuAsn>

      1160      1170      1180      1190      1200
         *    *    *    *    *    *    *    *    *    *
CTTGCATGAG GAGGAGCATG TCCTGCTCAT GGCCATCTGC ATCGTCTCCC
GAACGTACTC CTCCTCGTAC AGGACGAGTA CCGGTAGACG TAGCAGAGGG
 LeuHisGlu GluGluHis ValLeuLeuMet AlaIleCys IleValSer>

      1210      1220      1230      1240      1250
         *    *    *    *    *    *    *    *    *    *
CAGATCGTCC TGGGGTGCAG GACGCCGCGC TGATTGAGGC CATCCAGGAC
GTCTAGCAGG ACCCCACGTC CTGCGGCGCG ACTAACTCCG GTAGGTCCTG
ProAspArgPro GlyValGln AspAlaAla LeuIleGluAla IleGlnAsp>

      1260      1270      1280      1290      1300
         *    *    *    *    *    *    *    *    *    *
CGCCTGTCCA ACACACTGCA GACGTACATC CGCTGCCGCC ACCCGCCCCC
GCGGACAGGT TGTGTGACGT CTGCATGTAG GCGACGGCGG TGGGCGGGGG
ArgLeuSer AsnThrLeuGln ThrTyrIle ArgCysArg HisProProPro>
```

FIG. 5D

```
       1310       1320       1330       1340       1350
     *    *     *    *     *    *     *    *     *    *
GGGCAGCCAC CTGCTCTATG CCAAGATGAT CCAGAAGCTA GCCGACCTGC
CCCGTCGGTG GACGAGATAC GGTTCTACTA GGTCTTCGAT CGGCTGGACG
 GlySerHis LeuLeuTyr AlaLysMetIle GlnLysLeu AlaAspLeu>

       1360       1370       1380       1390       1400
     *    *     *    *     *    *     *    *     *    *
GCAGCCTCAA TGAGGAGCAC TCCAAGCAGT ACCGCTGCCT CTCCTTCCAG
CGTCGGAGTT ACTCCTCGTG AGGTTCGTCA TGGCGACGGA GAGGAAGGTC
ArgSerLeuAsn GluGluHis SerLysGln TyrArgCysLeu SerPheGln>

       1410       1420       1430       1440       1450
     *    *     *    *     *    *     *    *     *    *
CCTGAGTGCA GCATGAAGCT AACGCCCCTT GTGCTCGAAG TGTTTGGCAA
GGACTCACGT CGTACTTCGA TTGCGGGGAA CACGAGCTTC ACAAACCGTT
ProGluCys SerMetLysLeu ThrProLeu ValLeuGlu ValPheGlyAsn>

       1460
     *    *
TGAGATCTCC TGA (SEQ ID NO:2)
ACTCTAGAGG ACT (SEQ ID NO:17)
 GluIleSer ***>(SEQ ID NO:9)
```

FIG. 6A

Transcript 9
(Sequence range: 1 to 1382)

```
        10         20         30         40         50
     *    *     *    *     *    *     *    *     *    *
GTTTCCTTCT TCTGTCGGGG CGCCTTGGCA TGGAGTGGAG GAATAAGAAA
CAAAGGAAGA AGACAGCCCC GCGGAACCGT ACCTCACCTC CTTATTCTTT
                                MetGluTrpArg AsnLysLys>

        60         70         80         90        100
     *    *     *    *     *    *     *    *     *    *
AGGAGCGATT GGCTGTCGAT GGTGCTCAGA ACTGCTGGAG TGGAGGGGAT
TCCTCGCTAA CCGACAGCTA CCACGAGTCT TGACGACCTC ACCTCCCCTA
ArgSerAsp TrpLeuSerMet ValLeuArg ThrAlaGly ValGluGlyMet>

       110        120        130        140        150
     *    *     *    *     *    *     *    *     *    *
GGAGGCAATG GCGGCCAGCA CTTCCCTGCC TGACCCTGGA GACTTTGACC
CCTCCGTTAC CGCCGGTCGT GAAGGGACGG ACTGGGACCT CTGAAACTGG
 GluAlaMet AlaAlaSer ThrSerLeuPro AspProGly AspPheAsp>

       160        170        180        190        200
     *    *     *    *     *    *     *    *     *    *
GGAACGTGCC CCGGATCTGT GGGGTGTGTG GAGACCGAGC CACTGGCTTT
CCTTGCACGG GGCCTAGACA CCCCACACAC CTCTGGCTCG GTGACCGAAA
ArgAsnValPro ArgIleCys GlyValCys GlyAspArgAla ThrGlyPhe>

       210        220        230        240        250
     *    *     *    *     *    *     *    *     *    *
CACTTCAATG CTATGACCTG TGAAGGCTGC AAAGGCTTCT TCAGGCGAAG
GTGAAGTTAC GATACTGGAC ACTTCCGACG TTTCCGAAGA AGTCCGCTTC
HisPheAsn AlaMetThrCys GluGlyCys LysGlyPhe PheArgArgSer>

       260        270        280        290        300
     *    *     *    *     *    *     *    *     *    *
CATGAAGCGG AAGGCACTAT TCACCTGCCC CTTCAACGGG GACTGCCGCA
GTACTTCGCC TTCCGTGATA AGTGGACGGG GAAGTTGCCC CTGACGGCGT
 MetLysArg LysAlaLeu PheThrCysPro PheAsnGly AspCysArg>

       310        320        330        340        350
     *    *     *    *     *    *     *    *     *    *
TCACCAAGGA CAACCGACGC CACTGCCAGG CCTGCCGGCT CAAACGCTGT
AGTGGTTCCT GTTGGCTGCG GTGACGGTCC GGACGGCCGA GTTTGCGACA
IleThrLysAsp AsnArgArg HisCysGln AlaCysArgLeu LysArgCys>

       360        370        380        390        400
     *    *     *    *     *    *     *    *     *    *
GTGGACATCG GCATGATGAA GGAGTTCATT CTGACAGATG AGGAAGTGCA
CACCTGTAGC CGTACTACTT CCTCAAGTAA GACTGTCTAC TCCTTCACGT
ValAspIle GlyMetMetLys GluPheIle LeuThrAsp GluGluValGln>
```

FIG. 6B

```
        410       420       430       440       450
     *    *    *    *    *    *    *    *    *    *
GAGGAAGCGG GAGATGATCC TGAAGCGGAA GGAGGAGGAG GCCTTGAAGG
CTCCTTCGCC CTCTACTAGG ACTTCGCCTT CCTCCTCCTC CGGAACTTCC
 ArgLysArg GluMetIle LeuLysArgLys GluGluGlu AlaLeuLys>

        460       470       480       490       500
     *    *    *    *    *    *    *    *    *    *
ACAGTCTGCG GCCCAAGCTG TCTGAGGAGC AGCAGCGCAT CATTGCCATA
TGTCAGACGC CGGGTTCGAC AGACTCCTCG TCGTCGCGTA GTAACGGTAT
AspSerLeuArg ProLysLeu SerGluGlu GlnGlnArgIle IleAlaIle>

        510       520       530       540       550
     *    *    *    *    *    *    *    *    *    *
CTGCTGGACG CCCACCATAA GACCTACGAC CCCACCTACT CCGACTTCTG
GACGACCTGC GGGTGGTATT CTGGATGCTG GGGTGGATGA GGCTGAAGAC
LeuLeuAsp AlaHisHisLys ThrTyrAsp ProThrTyr SerAspPheCys>

        560       570       580       590       600
     *    *    *    *    *    *    *    *    *    *
CCAGTTCCGG CCTCCAGTTC GTGTGAATGA TGGTGGAGGG AGCCATCCTT
GGTCAAGGCC GGAGGTCAAG CACACTTACT ACCACCTCCC TCGGTAGGAA
 GlnPheArg ProProVal ArgValAsnAsp GlyGlyGly SerHisPro>

        610       620       630       640       650
     *    *    *    *    *    *    *    *    *    *
CCAGGCCCAA CTCCAGACAC ACTCCCAGCT TCTCTGGGGA CTCCTCCTCC
GGTCCGGGTT GAGGTCTGTG TGAGGGTCGA AGAGACCCCT GAGGAGGAGG
SerArgProAsn SerArgHis ThrProSer PheSerGlyAsp SerSerSer>

        660       670       680       690       700
     *    *    *    *    *    *    *    *    *    *
TCCTGCTCAG ATCACTGTAT CACCTCTTCA GACATGATGG ACTCGTCCAG
AGGACGAGTC TAGTGACATA GTGGAGAAGT CTGTACTACC TGAGCAGGTC
SerCysSer AspHisCysIle ThrSerSer AspMetMet AspSerSerSer>

        710       720       730       740       750
     *    *    *    *    *    *    *    *    *    *
CTTCTCCAAT CTGGATCTGA GTGAAGAAGA TTCAGATGAC CCTTCTGTGA
GAAGAGGTTA GACCTAGACT CACTTCTTCT AAGTCTACTG GGAAGACACT
 PheSerAsn LeuAspLeu SerGluGluAsp SerAspAsp ProSerVal>

        760       770       780       790       800
     *    *    *    *    *    *    *    *    *    *
CCCTAGAGCT GTCCCAGCTC TCCATGCTGC CCCACCTGGC TGACCTGGTC
GGGATCTCGA CAGGGTCGAG AGGTACGACG GGGTGGACCG ACTGGACCAG
ThrLeuGluLeu SerGlnLeu SerMetLeu ProHisLeuAla AspLeuVal>

        810       820       830       840       850
     *    *    *    *    *    *    *    *    *    *
AGTTACAGCA TCCAAAAGGT CATTGGCTTT GCTAAGATGA TACCAGGATT
TCAATGTCGT AGGTTTTCCA GTAACCGAAA CGATTCTACT ATGGTCCTAA
SerTyrSer IleGlnLysVal IleGlyPhe AlaLysMet IleProGlyPhe>
```

FIG. 6C

```
        860       870       880       890       900
          *         *         *         *         *
CAGAGACCTC ACCTCTGAGG ACCAGATCGT ACTGCTGAAG TCAAGTGCCA
GTCTCTGGAG TGGAGACTCC TGGTCTAGCA TGACGACTTC AGTTCACGGT
 ArgAspLeu ThrSerGlu AspGlnIleVal LeuLeuLys SerSerAla>

        910       920       930       940       950
          *         *         *         *         *
TTGAGGTCAT CATGTTGCGC TCCAATGAGT CCTTCACCAT GGACGACATG
AACTCCAGTA GTACAACGCG AGGTTACTCA GGAAGTGGTA CCTGCTGTAC
IleGluValIle MetLeuArg SerAsnGlu SerPheThrMet AspAspMet>

        960       970       980       990      1000
          *         *         *         *         *
TCCTGGACCT GTGGCAACCA AGACTACAAG TACCGCGTCA GTGACGTGAC
AGGACCTGGA CACCGTTGGT TCTGATGTTC ATGGCGCAGT CACTGCACTG
SerTrpThr CysGlyAsnGln AspTyrLys TyrArgVal SerAspValThr>

       1010      1020      1030      1040      1050
          *         *         *         *         *
CAAAGCCGGA CACAGCCTGG AGCTGATTGA GCCCCTCATC AAGTTCCAGG
GTTTCGGCCT GTGTCGGACC TCGACTAACT CGGGGAGTAG TTCAAGGTCC
 LysAlaGly HisSerLeu GluLeuIleGlu ProLeuIle LysPheGln>

       1060      1070      1080      1090      1100
          *         *         *         *         *
TGGGACTGAA GAAGCTGAAC TTGCATGAGG AGGAGCATGT CCTGCTCATG
ACCCTGACTT CTTCGACTTG AACGTACTCC TCCTCGTACA GGACGAGTAC
ValGlyLeuLys LysLeuAsn LeuHisGlu GluGluHisVal LeuLeuMet>

       1110      1120      1130      1140      1150
          *         *         *         *         *
GCCATCTGCA TCGTCTCCCC AGATCGTCCT GGGGTGCAGG ACGCCGCGCT
CGGTAGACGT AGCAGAGGGG TCTAGCAGGA CCCCACGTCC TGCGGCGCGA
AlaIleCys IleValSerPro AspArgPro GlyValGln AspAlaAlaLeu>

       1160      1170      1180      1190      1200
          *         *         *         *         *
GATTGAGGCC ATCCAGGACC GCCTGTCCAA CACACTGCAG ACGTACATCC
CTAACTCCGG TAGGTCCTGG CGGACAGGTT GTGTGACGTC TGCATGTAGG
 IleGluAla IleGlnAsp ArgLeuSerAsn ThrLeuGln ThrTyrIle>

       1210      1220      1230      1240      1250
          *         *         *         *         *
GCTGCCGCCA CCCGCCCCCG GGCAGCCACC TGCTCTATGC CAAGATGATC
CGACGGCGGT GGGCGGGGGC CCGTCGGTGG ACGAGATACG GTTCTACTAG
ArgCysArgHis ProProPro GlySerHis LeuLeuTyrAla LysMetIle>

       1260      1270      1280      1290      1300
          *         *         *         *         *
CAGAAGCTAG CCGACCTGCG CAGCCTCAAT GAGGAGCACT CCAAGCAGTA
GTCTTCGATC GGCTGGACGC GTCGGAGTTA CTCCTCGTGA GGTTCGTCAT
GlnLysLeu AlaAspLeuArg SerLeuAsn GluGluHis SerLysGlnTyr>
```

FIG. 6D

```
       1310      1320      1330      1340      1350
          *         *         *         *         *
CCGCTGCCTC TCCTTCCAGC CTGAGTGCAG CATGAAGCTA ACGCCCCTTG
GGCGACGGAG AGGAAGGTCG GACTCACGTC GTACTTCGAT TGCGGGGAAC
 ArgCysLeu SerPheGln ProGluCysSer MetLysLeu ThrProLeu>

       1360      1370      1380
          *         *         *
TGCTCGAAGT GTTTGGCAAT GAGATCTCCT GA (SEQ ID NO:3)
ACGAGCTTCA CAAACCGTTA CTCTAGAGGA CT (SEQ ID NO:18)
ValLeuGluVal PheGlyAsn GluIleSer ***> (SEQ ID NO:10)
```

FIG. 7A

Transcript 10
(Sequence Range: 1 to 1534)

```
        10         20         30         40         50
    *    *     *    *     *    *     *    *     *    *
GTTTCCTTCT TCTGTCGGGG CGCCTTGGCA TGGAGTGGAG GAATAAGAAA
CAAAGGAAGA AGACAGCCCC GCGGAACCGT ACCTCACCTC CTTATTCTTT
                                MetGluTrpArg AsnLysLys>

        60         70         80         90        100
    *    *     *    *     *    *     *    *     *    *
AGGAGCGATT GGCTGTCGAT GGTGCTCAGA ACTGCTGGAG TGGAGGGGAT
TCCTCGCTAA CCGACAGCTA CCACGAGTCT TGACGACCTC ACCTCCCCTA
ArgSerAsp TrpLeuSerMet ValLeuArg ThrAlaGly ValGluGlyMet>

       110        120        130        140        150
    *    *     *    *     *    *     *    *     *    *
GGAGGCAATG GCGGCCAGCA CTTCCCTGCC TGACCCTGGA GACTTTGACC
CCTCCGTTAC CGCCGGTCGT GAAGGGACGG ACTGGGACCT CTGAAACTGG
 GluAlaMet AlaAlaSer ThrSerLeuPro AspProGly AspPheAsp>

       160        170        180        190        200
    *    *     *    *     *    *     *    *     *    *
GGAACGTGCC CCGGATCTGT GGGGTGTGTG GAGACCGAGC CACTGGCTTT
CCTTGCACGG GGCCTAGACA CCCCACACAC CTCTGGCTCG GTGACCGAAA
ArgAsnValPro ArgIleCys GlyValCys GlyAspArgAla ThrGlyPhe>

       210        220        230        240        250
    *    *     *    *     *    *     *    *     *    *
CACTTCAATG CTATGACCTG TGAAGGCTGC AAAGGCTTCT TCAGGTGAGC
GTGAAGTTAC GATACTGGAC ACTTCCGACG TTTCCGAAGA AGTCCACTCG
HisPheAsn AlaMetThrCys GluGlyCys LysGlyPhe PheArg***(SEQ ID NO:11)

       260        270        280        290        300
    *    *     *    *     *    *     *    *     *    *
CCCCCTCCCA GGCTCTCCCC AGTGGAAAGG GAGGGAGAAG AAGCAAGGTG
GGGGGAGGGT CCGAGAGGGG TCACCTTTCC CTCCCTCTTC TTCGTTCCAC

       310        320        330        340        350
    *    *     *    *     *    *     *    *     *    *
TTTCCATGAA GGGAGCCCTT GCATTTTTCA CATCTCCTTC CTTACAATGT
AAAGGTACTT CCCTCGGGAA CGTAAAAAGT GTAGAGGAAG GAATGTTACA

       360        370        380        390        400
    *    *     *    *     *    *     *    *     *    *
CCATGGAACA TGCGGCGCTC ACAGCCACAG GAGCAGGAGG GTCTTGGCGA
GGTACCTTGT ACGCCGCGAG TGTCGGTGTC CTCGTCCTCC CAGAACCGCT
```

FIG. 7B

```
       410        420        430        440        450
    *    *     *    *     *    *     *    *     *    *
AGCATGAAGC GGAAGGCACT ATTCACCTGC CCCTTCAACG GGGACTGCCG
TCGTACTTCG CCTTCCGTGA TAAGTGGACG GGGAAGTTGC CCCTGACGGC

       460        470        480        490        500
    *    *     *    *     *    *     *    *     *    *
CATCACCAAG GACAACCGAC GCCACTGCCA GGCCTGCCGG CTCAAACGCT
GTAGTGGTTC CTGTTGGCTG CGGTGACGGT CCGGACGGCC GAGTTTGCGA

       510        520        530        540        550
    *    *     *    *     *    *     *    *     *    *
GTGTGGACAT CGGCATGATG AAGGAGTTCA TTCTGACAGA TGAGGAAGTG
CACACCTGTA GCCGTACTAC TTCCTCAAGT AAGACTGTCT ACTCCTTCAC

       560        570        580        590        600
    *    *     *    *     *    *     *    *     *    *
CAGAGGAAGC GGGAGATGAT CCTGAAGCGG AAGGAGGAGG AGGCCTTGAA
GTCTCCTTCG CCCTCTACTA GGACTTCGCC TTCCTCCTCC TCCGGAACTT

       610        620        630        640        650
    *    *     *    *     *    *     *    *     *    *
GGACAGTCTG CGGCCCAAGC TGTCTGAGGA GCAGCAGCGC ATCATTGCCA
CCTGTCAGAC GCCGGGTTCG ACAGACTCCT CGTCGTCGCG TAGTAACGGT

       660        670        680        690        700
    *    *     *    *     *    *     *    *     *    *
TACTGCTGGA CGCCCACCAT AAGACCTACG ACCCCACCTA CTCCGACTTC
ATGACGACCT GCGGGTGGTA TTCTGGATGC TGGGGTGGAT GAGGCTGAAG

       710        720        730        740        750
    *    *     *    *     *    *     *    *     *    *
TGCCAGTTCC GGCCTCCAGT TCGTGTGAAT GATGGTGGAG GGAGCCATCC
ACGGTCAAGG CCGGAGGTCA AGCACACTTA CTACCACCTC CCTCGGTAGG

       760        770        780        790        800
    *    *     *    *     *    *     *    *     *    *
TTCCAGGCCC AACTCCAGAC ACACTCCCAG CTTCTCTGGG GACTCCTCCT
AAGGTCCGGG TTGAGGTCTG TGTGAGGGTC GAAGAGACCC CTGAGGAGGA

       810        820        830        840        850
    *    *     *    *     *    *     *    *     *    *
CCTCCTGCTC AGATCACTGT ATCACCTCTT CAGACATGAT GGACTCGTCC
GGAGGACGAG TCTAGTGACA TAGTGGAGAA GTCTGTACTA CCTGAGCAGG

       860        870        880        890        900
    *    *     *    *     *    *     *    *     *    *
AGCTTCTCCA ATCTGGATCT GAGTGAAGAA GATTCAGATG ACCCTTCTGT
TCGAAGAGGT TAGACCTAGA CTCACTTCTT CTAAGTCTAC TGGGAAGACA

       910        920        930        940        950
    *    *     *    *     *    *     *    *     *    *
GACCCTAGAG CTGTCCCAGC TCTCCATGCT GCCCCACCTG GCTGACCTGG
CTGGGATCTC GACAGGGTCG AGAGGTACGA CGGGGTGGAC CGACTGGACC
```

FIG. 7C

```
        960        970        980        990       1000
          *    *     *    *     *    *     *    *     *    *
TCAGTTACAG CATCCAAAAG GTCATTGGCT TTGCTAAGAT GATACCAGGA
AGTCAATGTC GTAGGTTTTC CAGTAACCGA AACGATTCTA CTATGGTCCT

       1010       1020       1030       1040       1050
          *    *     *    *     *    *     *    *     *    *
TTCAGAGACC TCACCTCTGA GGACCAGATC GTACTGCTGA AGTCAAGTGC
AAGTCTCTGG AGTGGAGACT CCTGGTCTAG CATGACGACT TCAGTTCACG

       1060       1070       1080       1090       1100
          *    *     *    *     *    *     *    *     *    *
CATTGAGGTC ATCATGTTGC GCTCCAATGA GTCCTTCACC ATGGACGACA
GTAACTCCAG TAGTACAACG CGAGGTTACT CAGGAAGTGG TACCTGCTGT

       1110       1120       1130       1140       1150
          *    *     *    *     *    *     *    *     *    *
TGTCCTGGAC CTGTGGCAAC CAAGACTACA AGTACCGCGT CAGTGACGTG
ACAGGACCTG GACACCGTTG GTTCTGATGT TCATGGCGCA GTCACTGCAC

       1160       1170       1180       1190       1200
          *    *     *    *     *    *     *    *     *    *
ACCAAAGCCG GACACAGCCT GGAGCTGATT GAGCCCCTCA TCAAGTTCCA
TGGTTTCGGC CTGTGTCGGA CCTCGACTAA CTCGGGGAGT AGTTCAAGGT

       1210       1220       1230       1240       1250
          *    *     *    *     *    *     *    *     *    *
GGTGGGACTG AAGAAGCTGA ACTTGCATGA GGAGGAGCAT GTCCTGCTCA
CCACCCTGAC TTCTTCGACT TGAACGTACT CCTCCTCGTA CAGGACGAGT

       1260       1270       1280       1290       1300
          *    *     *    *     *    *     *    *     *    *
TGGCCATCTG CATCGTCTCC CCAGATCGTC CTGGGGTGCA GGACGCCGCG
ACCGGTAGAC GTAGCAGAGG GGTCTAGCAG GACCCCACGT CCTGCGGCGC

       1310       1320       1330       1340       1350
          *    *     *    *     *    *     *    *     *    *
CTGATTGAGG CCATCCAGGA CCGCCTGTCC AACACACTGC AGACGTACAT
GACTAACTCC GGTAGGTCCT GGCGGACAGG TTGTGTGACG TCTGCATGTA

       1360       1370       1380       1390       1400
          *    *     *    *     *    *     *    *     *    *
CCGCTGCCGC CACCCGCCCC CGGGCAGCCA CCTGCTCTAT GCCAAGATGA
GGCGACGGCG GTGGGCGGGG GCCCGTCGGT GGACGAGATA CGGTTCTACT

       1410       1420       1430       1440       1450
          *    *     *    *     *    *     *    *     *    *
TCCAGAAGCT AGCCGACCTG CGCAGCCTCA ATGAGGAGCA CTCCAAGCAG
AGGTCTTCGA TCGGCTGGAC GCGTCGGAGT TACTCCTCGT GAGGTTCGTC

       1460       1470       1480       1490       1500
          *    *     *    *     *    *     *    *     *    *
TACCGCTGCC TCTCCTTCCA GCCTGAGTGC AGCATGAAGC TAACGCCCCT
ATGGCGACGG AGAGGAAGGT CGGACTCACG TCGTACTTCG ATTGCGGGGA
```

FIG. 7D

```
      1510       1520       1530
    *    *     *    *     *    *
TGTGCTCGAA GTGTTTGGCA ATGAGATCTC CTGA (SEQ ID NO:4)
ACACGAGCTT CACAAACCGT TACTCTAGAG GACT (SEQ ID NO:19)
```

FIG. 8A

```
        10         20         30         40         50
         *          *          *          *          *
TGCGACCTTG GCGGTGAGCC TGGGGACAGG GGTGAGGCCA GAGACGGACG
ACGCTGGAAC CGCCACTCGG ACCCCTGTCC CCACTCCGGT CTCTGCCTGC

        60         70         80         90        100
         *          *          *          *          *
GACGCAGGGG CCCGGCCCAA GGCGAGGGAG AACAGCGGCA CTAAGGCAGA
CTGCGTCCCC GGGCCGGGTT CCGCTCCCTC TTGTCGCCGT GATTCCGTCT

       110        120        130        140        150
         *          *          *          *          *
AAGGAAGAGG GCGGTGTGTT CACCCGCAGC CCAATCCATC ACTCAGCAAC
TTCCTTCTCC CGCCACACAA GTGGGCGTCG GGTTAGGTAG TGAGTCGTTG

       160        170        180        190        200
         *          *          *          *          *
TCCTAGACGC TGGTAGAAAG TTCCTCCGAG GAGCCTGCCA TCCAGTCGTG
AGGATCTGCG ACCATCTTTC AAGGAGGCTC CTCGGACGGT AGGTCAGCAC

       210        220        230        240        250
         *          *          *          *          *
CGTGCAGAAG CCTTTGGGTC TGAAGTGTCT GTGAGACCTC ACAGAAGAGC
GCACGTCTTC GGAAACCCAG ACTTCACAGA CACTCTGGAG TGTCTTCTCG

       260        270        280        290        300
         *          *          *          *          *
ACCCCTGGGC TCCACTTACC TGCCCCCTGC TCCTTCAGGG ATGGAGGCAA
TGGGGACCCG AGGTGAATGG ACGGGGGACG AGGAAGTCCC TACCTCCGTT
                                            MetGluAla>

       310        320        330        340        350
         *          *          *          *          *
TGGCGGCCAG CACTTCCCTG CCTGACCCTG GAGACTTTGA CCGGAACGTG
ACCGCCGGTC GTGAAGGGAC GGACTGGGAC CTCTGAAACT GGCCTTGCAC
MetAlaAlaSer ThrSerLeu ProAspPro GlyAspPheAsp ArgAsnVal>

       360        370        380        390        400
         *          *          *          *          *
CCCCGGATCT GTGGGGTGTG TGGAGACCGA GCCACTGGCT TTCACTTCAA
GGGGCCTAGA CACCCCACAC ACCTCTGGCT CGGTGACCGA AAGTGAAGTT
ProArgIle CysGlyValCys GlyAspArg AlaThrGly PheHisPheAsn>

       410        420        430        440        450
         *          *          *          *          *
TGCTATGACC TGTGAAGGCT GCAAAGGCTT CTTCAGGCGA AGCATGAAGC
ACGATACTGG ACACTTCCGA CGTTTCCGAA GAAGTCCGCT TCGTACTTCG
 AlaMetThr CysGluGly CysLysGlyPhe PheArgArg SerMetLys>

       460        470        480        490        500
         *          *          *          *          *
GGAAGGCACT ATTCACCTGC CCCTTCAACG GGGACTGCCG CATCACCAAG
CCTTCCGTGA TAAGTGGACG GGGAAGTTGC CCCTGACGGC GTAGTGGTTC
ArgLysAlaLeu PheThrCys ProPheAsn GlyAspCysArg IleThrLys>
```

FIG. 8B

```
         510        520        530        540        550
           *          *          *          *          *
GACAACCGAC GCCACTGCCA GGCCTGCCGG CTCAAACGCT GTGTGGACAT
CTGTTGGCTG CGGTGACGGT CCGGACGGCC GAGTTTGCGA CACACCTGTA
AspAsnArg ArgHisCysGln AlaCysArg LeuLysArg CysValAspIle>

         560        570        580        590        600
           *          *          *          *          *
CGGCATGATG AAGGAGTTCA TTCTGACAGA TGAGGAAGTG CAGAGGAAGC
GCCGTACTAC TTCCTCAAGT AAGACTGTCT ACTCCTTCAC GTCTCCTTCG
 GlyMetMet LysGluPhe IleLeuThrAsp GluGluVal GlnArgLys>

         610        620        630        640        650
           *          *          *          *          *
GGGAGATGAT CCTGAAGCGG AAGGAGGAGG AGGCCTTGAA GGACAGTCTG
CCCTCTACTA GGACTTCGCC TTCCTCCTCC TCCGGAACTT CCTGTCAGAC
ArgGluMetIle LeuLysArg LysGluGlu GluAlaLeuLys AspSerLeu>

         660        670        680        690        700
           *          *          *          *          *
CGGCCCAAGC TGTCTGAGGA GCAGCAGCGC ATCATTGCCA TACTGCTGGA
GCCGGGTTCG ACAGACTCCT CGTCGTCGCG TAGTAACGGT ATGACGACCT
ArgProLys LeuSerGluGlu GlnGlnArg IleIleAla IleLeuLeuAsp>

         710        720        730        740        750
           *          *          *          *          *
CGCCCACCAT AAGACCTACG ACCCCACCTA CTCCGACTTC TGCCAGTTCC
GCGGGTGGTA TTCTGGATGC TGGGGTGGAT GAGGCTGAAG ACGGTCAAGG
 AlaHisHis LysThrTyr AspProThrTyr SerAspPhe CysGlnPhe>

         760        770        780        790        800
           *          *          *          *          *
GGCCTCCAGT TCGTGTGAAT GATGGTGGAG GGAGCCATCC TTCCAGGCCC
CCGGAGGTCA AGCACACTTA CTACCACCTC CCTCGGTAGG AAGGTCCGGG
ArgProProVal ArgValAsn AspGlyGly GlySerHisPro SerArgPro>

         810        820        830        840        850
           *          *          *          *          *
AACTCCAGAC ACACTCCCAG CTTCTCTGGG GACTCCTCCT CCTCCTGCTC
TTGAGGTCTG TGTGAGGGTC GAAGAGACCC CTGAGGAGGA GGAGGACGAG
AsnSerArg HisThrProSer PheSerGly AspSerSer SerSerCysSer>

         860        870        880        890        900
           *          *          *          *          *
AGATCACTGT ATCACCTCTT CAGACATGAT GGACTCGTCC AGCTTCTCCA
TCTAGTGACA TAGTGGAGAA GTCTGTACTA CCTGAGCAGG TCGAAGAGGT
 AspHisCys IleThrSer SerAspMetMet AspSerSer SerPheSer>

         910        920        930        940        950
           *          *          *          *          *
ATCTGGATCT GAGTGAAGAA GATTCAGATG ACCCTTCTGT GACCCTAGAG
TAGACCTAGA CTCACTTCTT CTAAGTCTAC TGGGAAGACA CTGGGATCTC
AsnLeuAspLeu SerGluGlu AspSerAsp AspProSerVal ThrLeuGlu>

         960        970        980        990       1000
           *          *          *          *          *
CTGTCCCAGC TCTCCATGCT GCCCCACCTG GCTGACCTGG TCAGTTACAG
GACAGGGTCG AGAGGTACGA CGGGGTGGAC CGACTGGACC AGTCAATGTC
LeuSerGln LeuSerMetLeu ProHisLeu AlaAspLeu ValSerTyrSer>
```

FIG. 8C

```
        1010       1020       1030       1040       1050
           *          *          *          *          *
 CATCCAAAAG GTCATTGGCT TTGCTAAGAT GATACCAGGA TTCAGAGACC
 GTAGGTTTTC CAGTAACCGA AACGATTCTA CTATGGTCCT AAGTCTCTGG
  IleGlnLys ValIleGly PheAlaLysMet IleProGly PheArgAsp>

        1060       1070       1080       1090       1100
           *          *          *          *          *
 TCACCTCTGA GGACCAGATC GTACTGCTGA AGTCAAGTGC CATTGAGGTC
 AGTGGAGACT CCTGGTCTAG CATGACGACT TCAGTTCACG GTAACTCCAG
LeuThrSerGlu AspGlnIle ValLeuLeu LysSerSerAla IleGluVal>

        1110       1120       1130       1140       1150
           *          *          *          *          *
 ATCATGTTGC GCTCCAATGA GTCCTTCACC ATGGACGACA TGTCCTGGAC
 TAGTACAACG CGAGGTTACT CAGGAAGTGG TACCTGCTGT ACAGGACCTG
 IleMetLeu ArgSerAsnGlu SerPheThr MetAspAsp MetSerTrpThr>

        1160       1170       1180       1190       1200
           *          *          *          *          *
 CTGTGGCAAC CAAGACTACA AGTACCGCGT CAGTGACGTG ACCAAAGCCG
 GACACCGTTG GTTCTGATGT TCATGGCGCA GTCACTGCAC TGGTTTCGGC
  CysGlyAsn GlnAspTyr LysTyrArgVal SerAspVal ThrLysAla>

        1210       1220       1230       1240       1250
           *          *          *          *          *
 GACACAGCCT GGAGCTGATT GAGCCCCTCA TCAAGTTCCA GGTGGGACTG
 CTGTGTCGGA CCTCGACTAA CTCGGGGAGT AGTTCAAGGT CCACCCTGAC
GlyHisSerLeu GluLeuIle GluProLeu IleLysPheGln ValGlyLeu>

        1260       1270       1280       1290       1300
           *          *          *          *          *
 AAGAAGCTGA ACTTGCATGA GGAGGAGCAT GTCCTGCTCA TGGCCATCTG
 TTCTTCGACT TGAACGTACT CCTCCTCGTA CAGGACGAGT ACCGGTAGAC
 LysLysLeu AsnLeuHisGlu GluGluHis ValLeuLeu MetAlaIleCys>

        1310       1320       1330       1340       1350
           *          *          *          *          *
 CATCGTCTCC CCAGATCGTC CTGGGGTGCA GGACGCCGCG CTGATTGAGG
 GTAGCAGAGG GGTCTAGCAG GACCCCACGT CCTGCGGCGC GACTAACTCC
  IleValSer ProAspArg ProGlyValGln AspAlaAla LeuIleGlu>

        1360       1370       1380       1390       1400
           *          *          *          *          *
 CCATCCAGGA CCGCCTGTCC AACACACTGC AGACGTACAT CCGCTGCCGC
 GGTAGGTCCT GGCGGACAGG TTGTGTGACG TCTGCATGTA GGCGACGGCG
AlaIleGlnAsp ArgLeuSer AsnThrLeu GlnThrTyrIle ArgCysArg>

        1410       1420       1430       1440       1450
           *          *          *          *          *
 CACCCGCCCC CGGGCAGCCA CCTGCTCTAT GCCAAGATGA TCCAGAAGCT
 GTGGGCGGGG GCCCGTCGGT GGACGAGATA CGGTTCTACT AGGTCTTCGA
 HisProPro ProGlySerHis LeuLeuTyr AlaLysMet IleGlnLysLeu>

        1460       1470       1480       1490       1500
           *          *          *          *          *
 AGCCGACCTG CGCAGCCTCA ATGAGGAGCA CTCCAAGCAG TACCGCTGCC
 TCGGCTGGAC GCGTCGGAGT TACTCCTCGT GAGGTTCGTC ATGGCGACGG
  AlaAspLeu ArgSerLeu AsnGluGluHis SerLysGln TyrArgCys>
```

FIG. 8D

```
       1510        1520        1530        1540        1550
          *           *           *           *           *
 TCTCCTTCCA GCCTGAGTGC AGCATGAAGC TAACGCCCCT TGTGCTCGAA
 AGAGGAAGGT CGGACTCACG TCGTACTTCG ATTGCGGGGA ACACGAGCTT
LeuSerPheGln ProGluCys SerMetLys LeuThrProLeu ValLeuGlu>

       1560        1570
          *           *
 GTGTTTGGCA ATGAGATCTC CTGA (SEQ ID NO:7)
 CACAAACCGT TACTCTAGAG GACT (SEQ ID NO:20)
 ValPheGly AsnGluIleSer ***> (SEQ ID NO:12)
```

ISOFORMS OF THE HUMAN VITAMIN D RECEPTOR

FIELD OF THE INVENTION

The present invention relates to isolated polynucleotide molecules which encode novel isoforms of the human Vitamin D receptor (hVDR) or variant transcripts for hVDR. The polynucleotide molecules may be utilised in, for example, methods of screening compounds for VDR agonists and/or antagonists.

BACKGROUND OF THE INVENTION

The active hormonal form of vitamin D, 1,25-dihydroxyvitamin $D_3$ (1.25$(OH)_2D_3$), has a central role in calcium and phosphate homeostasis, and the maintenance of bone. Apart from these calcitropic effects, 1,25-$(OH)_2D_3$ has been shown to play a role in controlling cell growth and differentiation in many target tissues. The effects of 1,25-$(OH)_2D_3$ are mediated by a specific receptor protein, the vitamin D receptor (VDR), a member of the nuclear receptor superfamily of transcriptional regulators which also includes steroid, thyroid and retinoid receptors as well as a growing number of orphan receptors. Upon binding hormone the VDR regulates gene expression by direct interaction with specific sequence elements in the promotor regions of hormone responsive target genes. This transactivation or repression involves multiple interactions with other protein cofactors, heterodimerisation partners and the transcription machinery.

Although a cDNA encoding the human VDR was cloned in 1988 (1), little has been documented characterising the gene structure and pattern of transcription since that time. The regulation of VDR abundance is one potentially important mechanism for modulating 1.25-$(OH)_2D_3$ responsiveness in target cells. It is also possible that VDR has a role in non-transcriptional pathways, perhaps via localization to a non-nuclear compartment and/or interaction with components of other signalling pathways. However, the question of how VDRs are targetted to different cell types and how they are regulated remains unresolved. There have been many reports in the literature describing translational or transcriptional control of VDR levels, both homologously and heterologously, mostly in non-human systems.

A recent study (2) showed that in the kidney, alternative splicing of human VDR transcripts transcribed from a GC rich promotor generates several transcripts which vary only in their 5' UTRs. The present inventors have now identified further upstream exons of the VDR gene which generate 5' variant transcripts, suggesting that the expression of the VDR gene is regulated by more than one promoter. A subset of these transcripts is expressed in a restricted tissue-specific pattern and further variant transcripts have the potential to encode an N-terminally variant protein. These results may have implications for understanding the actions of 1,25-$(OH)_2D_3$ in different tissues and cell types, and the possibility that N-terminally variant VDR proteins may be produced has implications for altered activities such as transactivation function or subcellular localisation of the receptor protein. Furthermore, these variants, by their level, tissue specificity, subcellular localisation and functional activity, may yield targets for pharmaceutical intervention. The variants may also be useful in screening potential analogs and/or antagonists of vitamin D compounds.

DISCLOSURE OF THE INVENTION

In a first aspect, the invention provides an isolated polynucleotide molecule encoding a human Vitamin D receptor (hVDR) isoform, said polynucleotide molecule comprising a nucleotide sequence which includes sequence that substantially corresponds or is functionally equivalent to that of exon 1d of the human VDR gene.

Exon 1d (referred to as exon 1b in the Australian Provisional Patent Specification No. PO9500) is a 96 bp exon located 296 bp downstream from exon 1a (2). The sequence of exon 1d is:

```
                                                (SEQ ID NO: 1)
5'GTTTCCTTCTTCTGTCGGGGCGCCTTGGCATGGAGTGGAGGAATAAGA
AAAGGAGCGATTGGCTGTCGATGGTGCTCAGAACTGCTGGAGTGGAGG
3'.
```

The nucleotide sequence of the polynucleotide molecule of the first aspect of the invention, preferably does not include sequence corresponding to that of exon 1a, exon 1f and/or exon 1e. However, the nucleotide sequence of the polynucleotide molecule of the first aspect of the invention, may or may not include sequence that substantially corresponds or is functionally equivalent to that of exon 1b and/or exon 1c.

Preferably, the polynucleotide molecule of the first aspect comprises a nucleotide sequence which includes;

(i) sequence that substantially corresponds or is functionally equivalent to that of exons 1d, 1c and 2-9 and encodes a VDR isoform of approximately 477 amino acids, (ii) sequence that substantially corresponds or is functionally equivalent to that of exons 1d and 2-9 and encodes a VDR isoform of approximately 450 amino acids, or (iii) sequence that substantially corresponds or is functionally equivalent to that of exons 1d and 2-9 and further includes a 152 bp intronic sequence, and encodes a truncated VDR isoform of approximately 72 amino acids.

Most preferably, the polynucleotide molecule of the first aspect of the invention comprises a nucleotide sequence substantially corresponding to that shown as SEQ ID NO: 2, SEQ ID NO: 3 or SEQ ID NO: 4.

In a second aspect, the invention provides an isolated polynucleotide molecule encoding a human Vitamin D receptor (hVDR), said polynucleotide molecule comprising a nucleotide sequence which includes sequence that substantially corresponds to that of exon 1f and/or 1e of the human VDR gene.

Exon 1f is a 207bp exon located more than 9 kb upstream from exon 1a (2) bp upstream from exon 1c(8). The sequence of exon 1f is:

```
                                                (SEQ ID NO: 5)
5'TGCGACCTTGGCGGTGAGCCTGGGGACAGGGGTGAGGCCAGAGACGGA
CGGACGCAGGGGCCCGGCCCAAGGCGAGGGAGAACAGCGGCACTAAGGCA
GAAAGGAAGAGGGCGGTGTGTTCACCCGCAGCCCAATCCATCACTCAGCA
ACTCCTAGACGCTGGTAGAAAGTTCCTCCGAGGAGCCTGCCATCCAGTCG
TGCGTGCAG3'
```

Exon 1e is a 157 bp exon located 1826 bp upstream from exon 1a (2). The sequence of exon 1e is:

```
                                        (SEQ ID NO: 6)
5'AGGCAGCATGAAACAGTGGGATGTGCAGAGAGAAGATCTGGGTCCAGT
AGCTCTGACACTCCTCAGCTGTAGAAACCTTGACAACTCTGCACATCAGT
TGTACAATGGAACGGTATTTTTTACTCTTCATGTCTGAAAAGGCTATGAT
AAAGATCAA3'
```

The nucleotide sequence of the polynucleotide molecule of the second aspect of the invention, preferably does not include sequence corresponding to that of exon 1a, 1d or 1b. However, the nucleotide sequence of the polynucleotide molecule of the second aspect of the invention, may or may not include sequence that substantially corresponds or is functionally equivalent to that of exon 1c.

Preferably, the nucleotide molecule of the second aspect comprises a nucleotide sequence which includes sequence that substantially corresponds or is functionally equivalent to that of exons 1f and 2-9.

Most preferably, the polynucleotide molecule of the first aspect of the invention comprises a nucleotide sequence substantially corresponding to that shown as SEQ ID NO: 7.

The polynucleotide molecule of the first or second aspects may be incorporated into plasmids or expression vectors (including viral vectors), which may then be introduced into suitable host cells (e.g. bacterial, yeast, insect and mammalian host cells). Such host cells may be used to express the VDR or functionally equivalent fragment thereof encoded by the isolated polynucleotide molecule.

Accordingly, in a third aspect, the present invention provides a host cell transformed with the polynucleotide molecule of the first or second aspect.

In a fourth aspect, the present invention provides a method of producing a VDR or a functionally equivalent fragment thereof, comprising culturing the host cell of the first or second aspect under conditions enabling the expression of the polynucleotide molecule and, optionally, recovering the VDR or functionally equivalent fragment thereof.

Preferably, the host cell is of mammalian origin. Preferred examples include NIH 3T3 and COS 7 cells.

In a preferred embodiment, the VDR or functionally equivalent fragment thereof is localised to a cell membrane or other subcellular compartment as distinct from a nuclear localisation.

The polynucleotide molecules of the first aspect of the invention encode novel VDR isoforms which may be of interest both clinically and commercially. By using the polynucleotide molecule of the present invention it is possible to obtain VDR isoform proteins or functionally equivalent fragments thereof in a substantially pure form.

Accordingly, in a fifth aspect, the present invention provides a human VDR isoform or functionally equivalent fragment thereof encoded by a polynucleotide molecule of the first aspect, said VDR isoform or functionally equivalent fragment thereof being in a substantially pure form.

In a sixth aspect, the present invention provides an antibody or antibody fragment capable of specifically binding to the VDR isoform of the fourth aspect.

The antibody may be monoclonal or polyclonal, however, it is presently preferred that the antibody is a monoclonal antibody. Suitable antibody fragments include Fab, $F(ab')_2$ and scFv.

In an eighth aspect, the present invention provides a non-human animal transformed with a polynucleotide molecule according to the first or second aspect of the invention.

In a seventh aspect, the invention provides a method for detecting agonist and/or antagonist compounds of a VDR isoform of the fourth aspect, comprising contacting said VDR isoform, functionally equivalent fragment thereof or a cell transformed with and expressing the polynucleotide molecule of the first aspect, with a test compound under conditions enabling the activation of the VDR isoform or functionally equivalent fragment thereof, and detecting an increase or decrease in the activity of the VDR isoform or functionally equivalent fragment thereof.

An increase or decrease in activity of the receptor or functionally equivalent fragment thereof may be detected by measuring changes in interactions with known cofactors (e.g. SRC-1, GRIP-1 and TFIIB) or unknown cofactors (e.g. through use of the yeast dual hybrid system).

In a ninth aspect, the present invention provides an oligonucleotide or polynucleotide probe comprising a nucleotide sequence of 10 or more nucleotides, the probe comprising a nucleotide sequence such that the probe specifically hybridises to the polynucleotide molecule of the first or second aspect under high stringency conditions (Sambrook et al., *Molecular Cloning: a laboratory manual*, Second Edition, Cold Spring Harbor Laboratory Press).

Preferably, the probe is labelled.

In a tenth aspect, the present invention provides an antisense polynucleotide molecule comprising a nucleotide sequence capable of specifically hybridising to an mRNA molecule which encodes a VDR encoded by the polynucleotide molecule of the first or second aspect, so as to prevent translation of the mRNA molecule.

Such antisense polynucleotide molecules may include a ribozyme region to catalytically inactivate mRNA to which it is hybridised.

The polynucleotide molecule of the first or second aspect of the invention may be a dominant negative mutant which encodes a gene product causing an altered phenotype by, for example, reducing or eliminating the activity of endogenous VDR.

In an eleventh aspect, the invention provides an isolated polynucleotide molecule comprising a nucleotide sequence substantially corresponding or, at least, showing >75% (preferably >85% or, even more preferably, >95%) sequence identity to:

```
(i)
                                        (SEQ ID NO: 5)
5'TGCGACCTTGGCGGTGAGCCTGGGGACAGGGGTGAGGCCAGAGACGGA
CGGACGCAGGGGCCCGGCCCAAGGCGAGGGAGAACAGCGGCACTAAGGCA
GAAAGGAAGAGGGCGGTGTGTTCACCCGCAGCCCAATCCATCACTCAGCA
ACTCCTAGACGCTGGTAGAAAGTTCCTCCGAGGAGCCTGCCATCCAGTCG
TGCGTGCAG3'(exon 1f),

(ii)
                                        (SEQ ID NO: 6)
5'AGGCAGCATGAAACAGTGGGATGTGCAGAGAGAAGATCTGGGTCCAGT
AGCTCTGACACTCCTCAGCTGTAGAAACCTTGACAACTCTGCACATGCAG
TTGTACAATGGAACGGTATTTTTTACTCTTCATGTCTGAAAAGGCTATGA
TAAAGATCAA3'(exon 1e),
or

(iii)
                                        (SEQ ID NO: 1)
5'GTTTCCTTCTTCTGTCGGGGCGCCTTGGCATGGAGTGGAGGAATAAGA
AAAGGAGCGATTGGCTGTCGATGGTGCTCAGAACTGCTGGAGTGGAGG3'
(exon 1d).
```

The polynucleotide molecules of the eleventh aspect may be useful as probes for the detection of VDR variant transcripts and as such may be useful in assessing cell or tissue-specific expression of variant transcripts.

The terms "substantially corresponds" and "substantially corresponding" as used herein in relation to nucleotide sequences is intended to encompass minor variations in the nucleotide sequence which due to degeneracy in the DNA code do not result in a substantial change in the encoded protein. Further, this term is intended to encompass other minor variations, in the sequence which may be required to enhance expression in a particular system but in which the variations do not result in a decrease in biological activity of the encoded protein.

The term "functionally equivalent" as used herein in relation to nucleotide sequences encoding a VDR isoform is intended to encompass nucleotide sequence variants of up to 5% sequence divergence (i.e. retaining 95% or more sequence identity) which encode VDR isoforms of substantially equivalent biological activity(ies) as said VDR isoform.

The term "functionally equivalent fragment" as used herein in respect of a VDR isoform is intended to encompass functional peptide and polypeptide fragments of said VDR isoform which include the domain or domains which bestow the biological activity characteristic of said VDR isoform.

The terms "comprise", "comprises" and "comprising" as used throughout the specification are intended to refer to the inclusion of a stated step, component or feature or group of steps, components or features with or without the inclusion of a further step, component or feature or group of steps, components or features.

The invention will hereinafter be further described by way of the following non-limiting example and accompanying figures.

BRIEF DESCRIPTION OF THE FIGURES

FIG. 4. Provides the nucleotide sequence of novel exons detected by 5' RACE: (A) exon 1b (SEQ ID NO: 8), (B) exon 1f (SEQ ID NO: 5) [P1f is indicated by an arrow above the sequence], (C) exon 1e (SEQ ID NO: 6), (D) exon 1d (SEQ ID NO: 1) [in-frame ATG codons are highlighted and P1d is indicated by an arrow above the sequence]. Intronic sequences are shown in lower case. Canonical splice site consensus sequences are indicated in bold. The transcription start sites for exons 1f and 1d were determined by the 5' termini of RACE clones. No intron sequence is shown 3' to exon 1f as cosmid clone J5 terminated in the intron between exons 1f and 1e.

FIGS. 5A-5D. Provides the nucleotide sequence corresponding to transcript 6 (see FIG. 1) (SEQ ID NO: 2), together with the predicted amino acid sequence (SEQ ID NO: 9) of the encoded protein. Nucleotides 1-96 correspond to exon 1d; nucleotides 97-1463 correspond to exons 1c to the stop codon in exon 9 (or nucleotides -83-1283 of the hVDR cDNA (1)).

FIG-6A-6D. Provides the nucleotide sequence corresponding to transcript 9 (see FIG. 1) (SEQ ID NO: 3), together with the predicted amino acid sequence (SEQ ID NO: 10) of the encoded protein. Nucleotides 1-96 correspond to exon 1 d; nucleotides 97 - 1382 correspond to exon 2 to the stop codon in exon 9 (or nucleotides -2 - 1283 of the hVDR cDNA (1)).

FIGS. 7A-7D. Provides the nucleotide sequence corresponding to transcript 10 (see FIG. 1) (SEQ ID NO: 4), together with the predicted amino acid sequence (SEQ ID NO: 11) of the encoded protein. Nucleotides 1-96 correspond to exon 1 d; nucleotides 97-244 correspond to exon 2; nucleotides 245-396 correspond to intronic sequence immediately 3' to exon 2; nucleotides 397-1534 correspond to exons 3 to the stop codon in exon 9 (or nucleotides 146-1283 of the hVDR cDNA (1)).

FIGS. 8A-8D. Provides the nucleotide sequence corresponding to transcript 11 (see FIG. 1) (SEQ ID NO: 7), together with the predicted amino acid sequence (SEQ ID NO: 12) of the encoded protein. Nucleotides 1-207 correspond to exon if; nucleotides 208-1574 correspond to exon 1c to the stop codon in exon 9 (or nucleotides -83-1283 of the hVDR cDNA (1)).

EXAMPLE

Experimental Procedures

Isolation and Characterisation of Genomic Clones

Figure 1A:
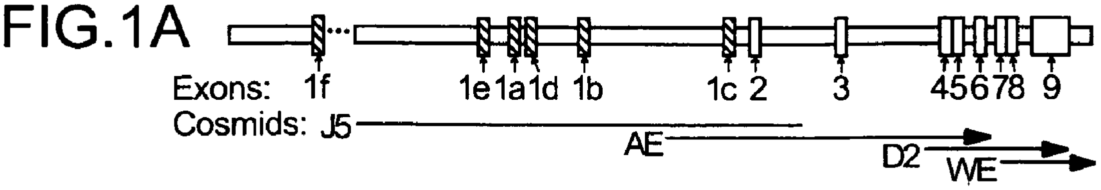
FIG. 1A Human VDR gene locus. Four overlapping cosmid clones were isolated from a human lymphocyte genomic library (Stratagene) and directly sequenced. Clone J5 extends from the 5' flanking region to intron 2; AB, from intron 1b to intron 5; D2, from intron 3 to the 3' UTR; WE, from intron 6 through the 3' flanking region. Sequence upstream of exon 1f was obtained by anchored PCR from genomic DNA.

A human lymphocyte cosmic library (Stratagene, La Jolla, Calif.) was screened using a 2.1 kb fragment of the hVDR cDNA encompassing the entire coding region but lacking the 3'UTR, a 241 bp PCR product spanning exons 1 to 3 of the human VDR cDNA, and a 303 bp PCR product spanning exons 3 and 4 of the hVDR cDNA, following standard colony hybridisation techniques. DNA probes were labelled by nick translation (Life Technologies, Gaithersburg, Md.) with [($\alpha^{32}$ P] dCTP. Positively hybridising colonies were picked and secondary and tertiary screens carried out until complete purification. Cosmid DNA from positive clones was purified (Qiagen), digested with different restriction enzymes and characterised by Southern blot analysis using specific [$\gamma^{32}$ P]ATP labelled oligonucleotides as probes. Cosmid clones were directly sequenced using dye-termination chemistry and automated fluorescent sequencing on an ABI Prism. 377 DNA Sequencer (Perkin-Elmer, Foster City, Calif.). Sequence upstream of the most 5' cosmid was obtained by anchored PCR from genomic DNA using commercially available anchor ligated DNA (Clontech, Palo Alto, Calif.).

Rapid Amplification of cDNA 5-prime Ends (5'-RACE)

Alternative 5' variants of the human VDR gene were identified by 5'RACE using commercially prepared anchor-ligated cDNA (Clontech) following the instructions of the manufacturer. Two rounds of PCR using nested reverse primers in exons 3 and 2 (P 1:5'ccgcttcatgcttcgcctgaagaagcc-3' (SEO ID NO: 23), P2:5'-tgcagaattcacaggtcatagcattgaag-3' (SEO ID NO: 24)) were carried out on a Corbett FTS-4000 Capillary Thermal Sequencer (Corbett Research, NSW, Australia). After 26 cycles of PCR, 2% of the primary reaction was reamplified for 31 cycles. The PCR products were cloned into PUC 18 and sequenced by the dideoxy chain termination method.

Cell-Culture

The embryonal kidney cell line, HEK-293, ail embryonic intestine cell line, Intestine-407 and WS 1, a foetal skin fibroblast cell line were all cultured in Eagle's MEM with Earle's BSS and supplemented with either 10% heat-inactivated FBS, 15% FBS or 10% FBS with non-essential amino acids, respectively. The osteosarcoma cell lines MG-63 and Saos-2 were cultured in Eagle's MEM with nonessential amino acids and 10% heat-inactivated FBS and McCoy's 5a medium with 15% FBS, respectively. The breast carcinoma cell line T47D and the colon carcinoma cell lines LIM 1863 and COLO 206F were cultured in RPMI medium supplemented with 0.2 IU bovine insulin/ill and 10% FBS, 5% FBS or 10% FBS, respectively. LIM 1863 were a gift from R. H. Whitehead (3). HK-2 kidney proximal tubule cells were grown in keratinocyte-serum free medium supplemented with 5 ng/mil recombinant EGF, 40 ug/ml bovine pituitary extract. BC1 foetal osteoblast-like cells were kindly donated by R. Mason (4) and were grown in Eagle's MEM with 5% FBS and 5 mg/L vitamin C. Unless otherwise stated all cell lines were obtained from the American Type Culture Collection (Manassas, Va.).

Reverse Transcriptase—PCR (RT-PCR)

Total RNA extracted from approximately $1.5\times10^3$ cells, from leukocytes prepared from 40 ml blood, or from human tissue using acid-phenol extraction was purified by using a guanidium isothiocyanate-cesium chloride step gradient.

First-strand cDNA was synthesized from 5 Tg of total RNA primed with random hexamers (Promega) using Superscript II reverse transcriptase (Life Technologies). One-tenth of the cDNA (2T1) was used for subsequent PCR, with 36 cycles of amplification, using exon-specific forward primers (exon 1a: corresponding to nucleotides 1-21 of hVDR cDNA (1);

```
                                          (SEQ ID NO: 25)
exon 1d:     5'-GGCTGTCGATGGTGCTCAGAAC-3';
                                          (SEQ ID NO: 26)
exon 1f:     5'-AAGTTCCTCCGAGGAGCCTGCC-3');
```

and a common reverse primer in exon 3 All RT-PCRs were repeated multiple times by using RNAIcDNA prepared at different times from multiple sources. Each PCR included an appropriate cDNA-negative control, and additional controls included RT-negative controls prepared alongside cDNA and RNA/cDNA prepared from VDR-negative cell lines. PCR products were separated on 2% agarose and visualized with ethidium bromide staining.

Functional Analysis of hVDR Gene Promoters

Sequences flanking exons 1a, 1d, and 1f (see FIG. 1A) were PCR-amplified by using Pfu polymerase (Stratagene) and cloned into the pGL3basic vector (Promega) upstream of the luciferase gene reporter. Promoter-reporter constructs were transfected into NIH 3T3 and COS 7 cells by using the standard calcium phosphate-precipitation method. Cells were seeded at $2.3\pm2.5\times10^{11}$ per 150-cm$^2$ flask the day before transfection. Several hours before the precipitates were added the medium was changed to DMEM with 2% charcoal-stripped FBS. Cells were exposed to precipitate for 16 h before subculturing and were harvested 24 h later. The parent vector pGL3basic was used as a promoterless control in these experiments and a simian virus 40 promoter-chloramphenicol acetyltransferase (CAT) gene reporter construct was cotransfected as an internal control for transfection efficiency in each case. The activity of each construct was corrected for transfection efficiency and for the activity of the pGL3 basic empty vector control and expressed as a percentage of the activity of the construct 1a (−488, +75). Luciferase and CAT assays were carried out in triplicate, and each construct was tested in transfection at least three times.

Results

Identification of Alternative 5' Variants of the hVDR Genie

Figure 1B:
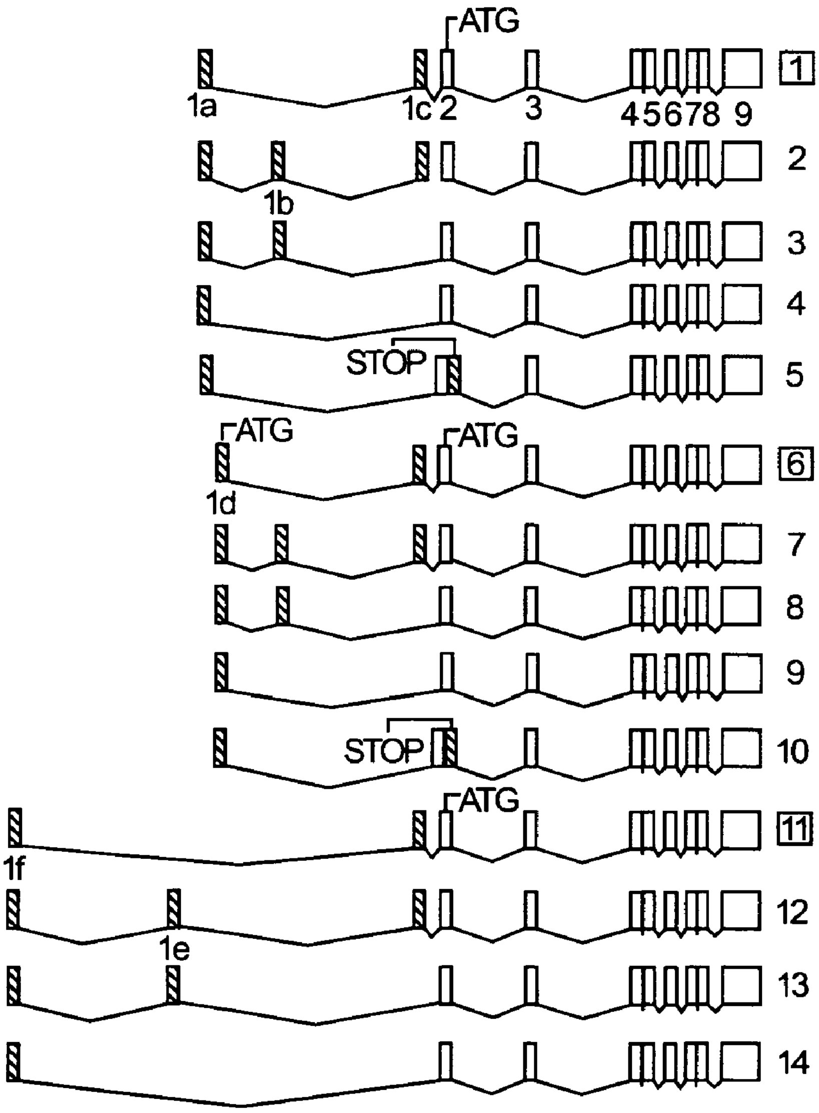
FIG. 1B Structure of hVDR transcripts. Transcripts 1-5 originate from exon 1a. Transcript 1 corresponds to the published cDNA (1). Transcripts 6-10 originate from exon 1d and transcripts 11-14 originate from exon 1f. Boxed numbers indicate the major transcript (based on the relative intensities of the multiple PCR products) within each exon-specific group of transcripts generated with a single primer set. While all transcripts have a translation initiation codon in exon 2, exon 1 d transcripts have the potential to initiate translation upstream in exon 1d, with transcripts 6 and 9 encoding VDR proteins with extended N termini.

Upstream exons were identified in human kidney VDR transcripts by 5' RACE (exons 1f, 1e, 1d, and 1b) and localized by sequencing of cosmid clones (FIG. 1A). To verify these results and to characterize the structure of the 5' end of the VDR gene, exon-specific forward primers were used with a common reverse primer in exon 3 to amplify specific VDR transcripts from human tissue and cell line RNA (FIG. 1B). The identity of these PCR products was verified by Southern blot and by cloning and sequencing. Five different VDR transcripts originating from exon 1a were identified. The major transcript (transcript 1 in FIG. 1B) corresponds to the published cDNA sequence (1). Three less-abundant forms (2, 3, and 4 in FIG. 1B) arise from alternative splicing of exon 1c and a novel 122-bp exon 1b into or out of the final transcript. These three valiant transcripts were described recently by Pike and colleagues (2). A fifth minor variant was identified (5 in FIG. 1B) that lacks exons 1b and 1c, but includes an extra 152 bp of intronic sequence immediately 3' to exon 2, potentially encoding a truncated protein as a result of an in-frame termination codon in intron 2.

Four more transcripts were characterized that originate from exon 1f, a novel 207-bp exon more than 9 kb upstream from exon 1a. The major 1f-containing transcript (11 in FIG. 1B) consists of exon 1f spliced immediately adjacent to exon 1c. Three less-abundant variants (12, 13, and 14 in FIG. 1B) arise from alternative splicing of exon 1c and a novel 159-bp exon 1e into or out of the final transcript. All these hVDR variants differ only in their 5' UTRs and encode identical proteins from translation initiation in exon 2.

Figure 1C:
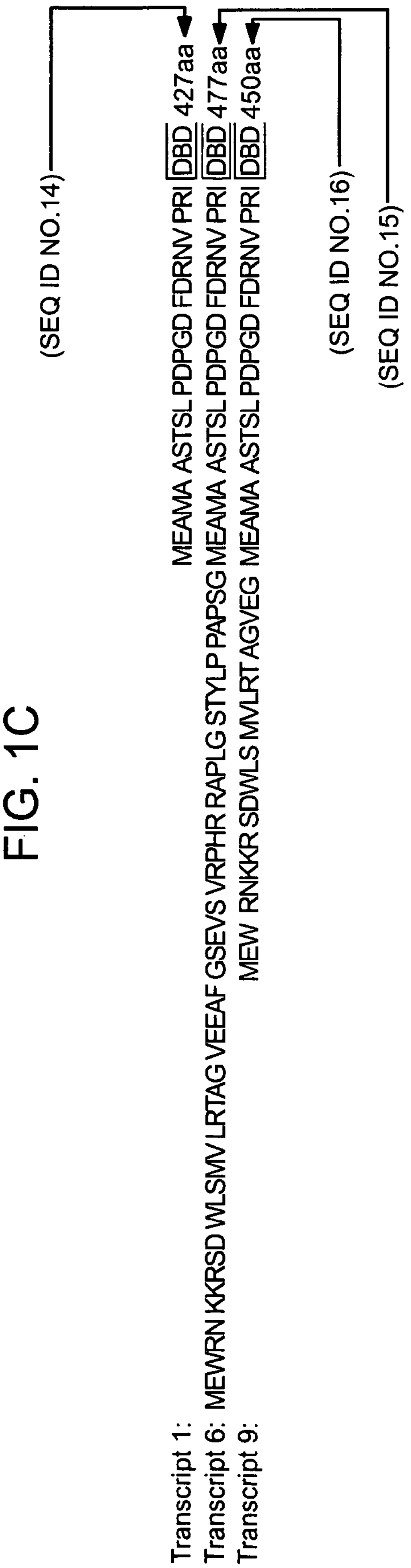
FIG. 1C N-terminal variant proteins encoded by novel hVDR transcripts. Transcript 1 corresponds to the published cDNA sequence (1) and encodes the 427-aa hVDR protein. Transcripts 6 and 9 code for a protein with an extra 50 an or 23 aa, respectively, at the N-terminal. The 23 an of the hVDR A/B domain are shown in bold.

Of considerable interest, another five hVDR transcripts were identified that originate from exon 1d, a novel 96-bp exon located 296 bp downstream from exon 1a. The major exon 1d-containing transcript (6 in FIG. 1B) utilizes exon 1d in place of exon 1a of the hVDR cDNA. Three minor variants (7, 8, and 9 in FIG. 1B) arise from alternative splicing of exons 1b and 1c into or out of the transcript, analogous to the exon 1a-containing variants 2, 3, and 4. A fifth minor variant transcript (10 in FIG. 1B) lacks exons 1b and 1c, but includes 152 bp of intron 2 analogous to the exon 1a-containing transcript 5, and also potentially encodes a truncated protein. Two of these exon 1d-containing hVDR transcripts encode an N-terminal variant form of the hVDR protein. Utilization of an ATG codon in exon 1d, which is in a favorable context and in-frame with the major translation start site in exon 2, would generate a protein with an additional 50 aa N-terminal to the ATG codon in exon 2 in the case of variant 6 or 23 aa in the case of variant 9 (FIG. 1C).

The relative level of expression of the different transcripts is difficult to address with PCR since relatively minor transcripts may be amplified. However, Southern blots of PCR products from the linear range of PCR amplification indicated that equivalent amounts of PCR product were accumulated after 26 cycles for exon 1a transcripts compared with 30 cycles for exon 1d transcripts, suggesting that 1d abundance is about 5% of that of 1a transcripts. This is consistent with the frequency of clones selected and sequenced from RACE analysis of two separate samples of kidney RNA: 1a (21/27; 78%), 1d (2/27; 7%), and 1f (4/27; 1596). RT-PCR with exon 1a-, 1d-, or 1f-specific forward primers and reverse primers in exons 7 or 9, followed by cloning and sequencing, suggests that these 5' variant transcripts are not associated with differences at the 3' end of the transcript.

Exon-Intron Organization of the hVDR Gene

Overlapping cosmid clones were isolated from a human lymphocyte genomic library and characterized by hybridization to exon-specific oligonucleotide probes (FIG. 1A). The exon-intron boundaries of the hVDR gene were determined by comparison of the genomic sequence from cosmid clones with the cDNA sequence. Upstream exons were localized in the VDR gene by sequencing cosmid clones, which extend approximately 7 kb into the intron between exons 1e and 1f, enabling verification of both their sequence and the presence of consensus splice donor/acceptor sites. Sequence upstream of exon 1f was obtained by anchored PCR from genomic DNA by using commercially available anchor-ligated DNA (CLONTECH). In total, the hVDR gene spans more than 60 kb and consists of at least 14 exons (FIG. 1A).

Tissue-Specific Expression of hVDR Transcripts

Figure 2:
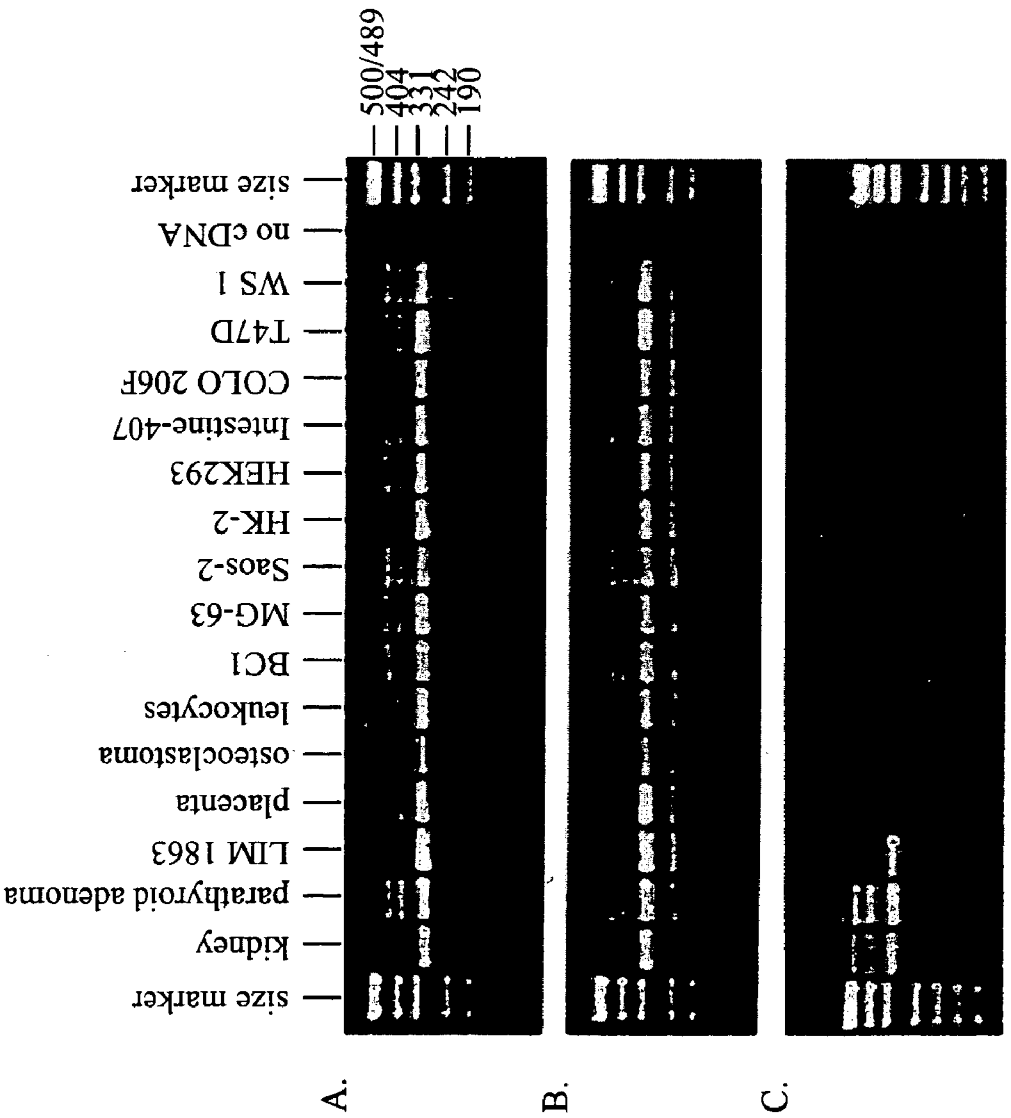
FIG. 2. RT-PCR analysis of expression of variant hVDR transcripts. (A) Exon 1a transcripts (220 bp, 301 bp, 342 bp, 372 bp, and 423 bp). (B) Exon 1d transcripts (224 bp, 305 bp, 346 bp, 376 bp, and 427 bp). (C) Exon 1f transcripts (228 bp, 309 bp, 387 bp, and 468 bp). RT-PCR was carried out with exon 1a-, 1d-, or 1f-specific forward primers and a common reverse primer in exon 3. The sizes of the PCR products and the pattern of bands are similar in A and B by virtue of the identical splicing pattern of exon 1a and 1d transcripts and the fact that primers were designed to generate PCR products of comparable sizes. All tissues and cell lines are human in origin.

The pattern of expression of variant hVDR transcripts was examined by RT-PCR in a variety of cell lines and tissues with exon 1a-, 1d-, or 1f-specific forward primers and a common reverse primer in exon 3. Exon 1a and 1d transcripts (FIG. 1B, variants 1-10) were coordinately expressed in all RNA samples analyzed (FIGS. 2A and B). Exon 1f transcripts (FIG. 1B, variants 11-14), however, were detected only in RNA from human kidney tissue (two separate samples), human parathyroid adenoma tissue, and an intestinal carcinoma cell line. LIM 1863 (FIG. 2C). Interestingly, these represent major target tissues for the calcitropic effects of vitamin D.

Functional Analysis of hVDR Gene Promoters

Figure 3:
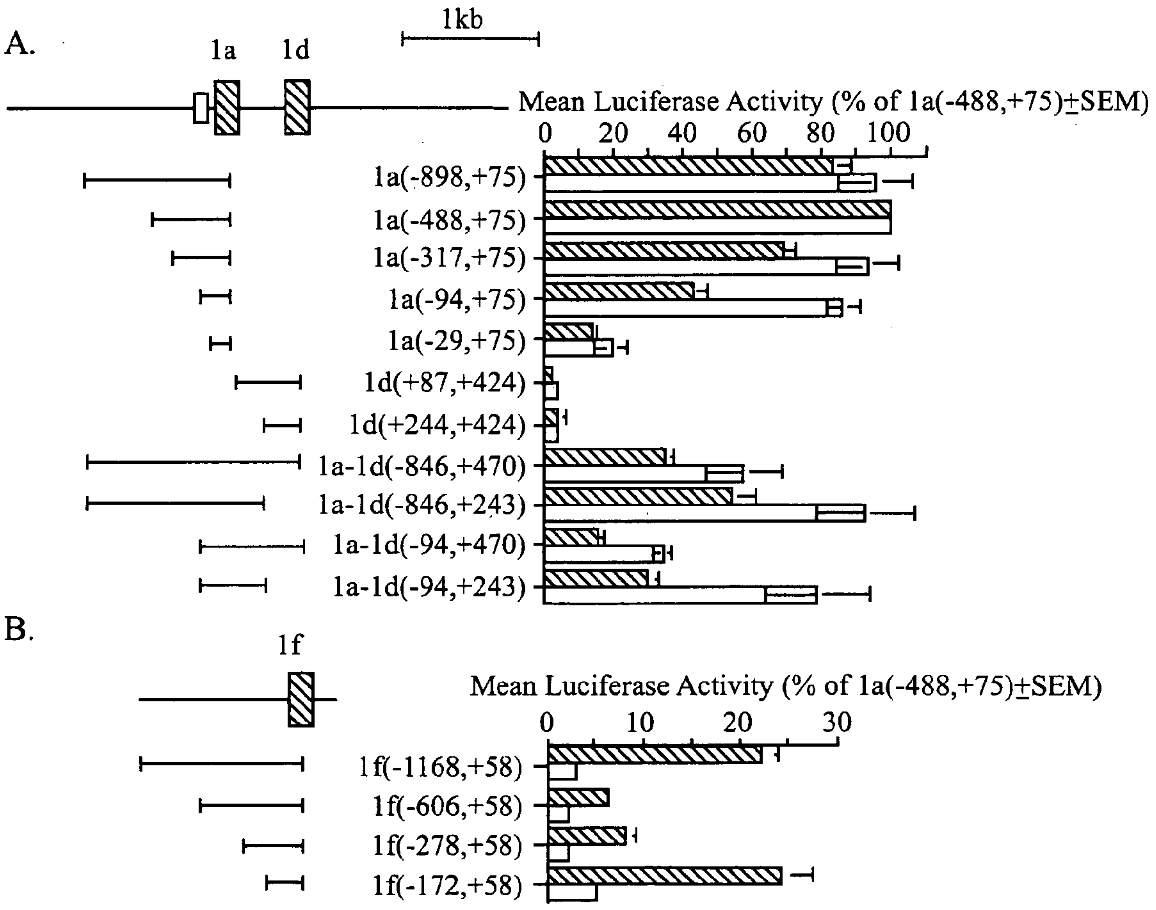
FIG. 3. Functional analysis of sequence-flanking exons 1a and 1d (A) and exon 1f (B) in NIH 3T3 (solid bars) and COS 7 cells (open bars). The parent vector pGL3basic was used as a promoterless control, and a promoter-chloramphenicol acetyltransferase (CAT) gene reporter construct was cotransfected as an internal control for transfection efficiency in each case. The activity of each construct was corrected for transfection efficiency and for the activity of the pGL3basic empty vector control and expressed as a percentage of the activity of the construct 1a (−488, +75) SEM of at least three separate transfections. Exon 1a and 1d flanking constructs are defined in relation to the transcription start site of exon 1a, designated 11, which lies 54 nt upstream of the published cDNA (1). Exon 1f flanking constructs are defined relative to the exon 1f transcription start site, designated 11. Transcription start sites were determined by the 5' termini of the longest RACE clones. The open box corresponds to the GC-rich region.

Promoter activities of the 5' flanking regions of exons 1a, 1d, and 1f were examined in NIH 3T3 and COS 7 cells (FIG. 3). Sequences flanking exon 1a exhibited high promoter activity in both cell lines (FIG. 3A). Maximum luciferase expression of 36- and 54-fold over the empty vector was attained for construct 1a (−488, +75) in NIH 3T3 and COS 7 cells, respectively. This activity could be attributed largely to a GC-rich region containing multiple consensus Sp1-binding motifs lying within 100 bp immediately adjacent to the transcription start site. This region alone, upstream of a luciferase reporter [construct 1a (−94, +75)], accounted for 43% of the maximum activity observed in NIH 3T3 cells and 86% of the maximum observed in COS 7 cells. The removal of this GC-rich region [construct 1a (−29, +75)] reduced luciferase activity to only 13% of the maximum in NIH 3T3 and 19% in COS 7 cells. Despite the fact that VDR transcripts that originated from exon 1d were identified, distinct promoter activity was not associated with sequences within 300 bp of exon 1d [constructs 1d (+87, +424) and 1d(+244, +424)]; rather, the sequence immediately adjacent to exon 1d may contain a suppressor element (FIG. 3A). Construct 1a-1d (−846, +470), spanning the 5' flanking regions of both exons 1a and 1d, resulted in only 42% and 60%, of the activity of 1a (−898, +75) in NIH 3T3 and COS 7 cells, whereas the 3' deletion of 227 bp restored luciferase activity to 65% and 97% of the activity of 1a (−898, +75), respectively. Similarly, the 5' truncated construct 1a-1d (−94, +470), spanning the 5' flanking regions of both 1a and 1d, resulted in only 35% and 40% of the activity of 1a (−94, +75), while a further 3' deletion of 227 bp restored luciferase activity to 69% and 91% of the activity of 1a (−94, +75) in NIH 3T3 and COS 7 cells. It is possible that transcription from exons 1a and 1d is driven by overlapping promoter regions rather than from two distinct promoters, as has been described for the mouse androgen receptor gene.

Sequence upstream of exon 1f showed significant promoter activity in NIH 3T3 cells of 22% of that of the most active construct, 1a (−488, +75), or 9-fold over pGL3basic [construct 1f (−1168, +58)] (FIG. 3B). A shorter construct [1f (−172, +58)] had similar activity, with evidence of a suppressor element (between nucleotides −278 and +172) able to repress luciferase activity by 70%. Interestingly, the same constructs were not active in COS 7 cells. This cell line-specific activity of exon 1f flanking sequences may reflect a requirement for tissue- or cell-specific protein factors.

Identification of VDR Isoforms in Whole Cell Lysates

The existence of a VDR isoform including exons 1d and 1c has been confirmed in cell lysates from multiple human, monkey, rat and mouse cell lines derived from kidney, intestine, liver and bone, by immunoprecipitation (using the anti-VDR 9A7 rat monoclonal antibody; Affinity Bioreagents Inc., Golden, Colo.) followed by Western blot analysis. The 1d- and 1c-exon-specific antibodies detected the same band in all immunoprecipitations.

Discussion

The present inventors have identified 5' variant transcripts of the hVDR that suggest the existence of alternative promoters. These transcripts may not have been discriminated in previous Northern analyses because of their similarity in size. Transcription initiation from exons 1a or 1f and alternative splicing generate VDR transcripts that vary in their 5' UTRs but encode the same 427-aa protein. Transcription initiation from exon 1d and alternative splicing generate hVDR transcripts with the potential to encode variant proteins with an additional 50 or 23 aa at the N terminals. There was no evidence that these 5' variants are associated with differences at the 3' end of the transcript. Although isoforms are common in other members of the nuclear receptor superfamily, the only evidence for isoforms of the hVDR is a common polymorphism in the triplet encoding the initiating methionine of the 427-aa form of the VDR that results in initiation of translation at an alternative start codon beginning at the 10th nucleotide down-stream, encoding a protein truncated by 3 aa at the N terminus (5). Similarly, two forms of the avian VDR, differing in size by 14 aa, are generated from a single transcript by alternative translation initiation (6), and in the rat a dominant-negative VDR is generated by intron retention (7).

Heterogeneity in the 5' region is a common feature of other nuclear receptor genes. Tissue-specific alternative-promoter usage generates multiple transcripts of the human estrogen receptor a (ERa), the human and rat mineralocorticoid receptors, and the mouse glucocorticoid receptor (GR), which differ in their 5' UTRs but code for identical proteins. However, other members of the nuclear receptor superfamily have multiple, functionally distinct isoforms arising from differential promoter usage and/or alternative splicing. The generation of N-terminal variant protein isoforms has been described for the progesterone receptor (PR), peroxisome proliferator-activated receptor ($PPAR_O$), and the retinoid and thyroid receptors. Some receptor isoforms exhibit differential promoter-specific transactivation activity. The N-terminal A/B regions of many nuclear receptor proteins possess a ligand-independent transactivation function (AF1). An AF1 domain has been demonstrated for the thyroid receptor bi (TRb1), ER, GR, PR, PPARg, and the retinoid receptors. The activity of the AF1 domain has been shown to vary in both a tissue- and promoter-specific manner. The N-terminal A/B region of nuclear receptors is the least-conserved domain across the family and between receptor subtypes, varying considerably both in length and sequence. The VDR, however, is unusual as its N-terminal A/B region is much shorter than that of other nuclear receptors, with only 23 aa N-terminal to the DNA-binding domain, and deletion of these residues seems to have no effect on VDR function. This region in other receptors is associated with optimal ligand-dependent transactivation and can interact directly with components of the basal transcription complex. Two stretches of basic amino acid residues, RNKKR (SEQ ID NO: 27) and RPHRR (SEQ ID NO: 28), in the predicted amino acid sequences of the variant hVDR N termini (FIG. 1C resemble nuclear localization signals. An N-terminal variant VDR protein therefore might exhibit different transactivation potential, possibly mediated by different protein interactions, or may specify a different subcellular localization. The tissue-specific expression of exon 1 f-containing transcripts is mediated by a distal promoter more than 9 kb upstream of exons 1 a and 1 d. Exon if transcripts were detected only in kidney tissue, parathyroid adenoma tissue, and an intestinal cell line, LIM 1863. It is interesting that these tissues represent major target tissues for the calcitropic effects of vitamin D. The absence of if-containing transcripts in two other kidney cell lines, HK-2 (proximal tubule) and HEK-293 (embryonal kidney), as well as one other embryonal intestinal cell line, Intestine-407, suggests that the expression of if transcripts is cell type-specific. The cell line-specific activity of exon if flanking sequences in promoter reporter assays may reflect a requirement for tissue- or cell-specific protein factors to mediate expression from this promoter.

This study has demonstrated that expression of the human VDR gene, which spans more than 60 kb and consists of 14 exons, is under complex transcriptional control by multiple promoters. The expression of multiple exon 1f transcripts is mediated by utilization of a distal tissue-specific promoter. Transcription from a proximal promoter, or promoters, generates multiple variant hVDR transcripts, two of which code for N-terminal variant proteins. Multiple, functionally distinct isoforms mediate the tissue- and/or developmental-specific effects of many members of the nuclear receptor superfamily. Although the actual relative abundance of the various transcripts and their levels of translation in vivo have not yet been characterized, the results suggest that major variant isoform of the hVDR exist. Differential regulation of these hVDR gene promoters and of alternative splicing of variant VDR transcripts may have implications for understanding the various actions of $1,25\text{-}(OH)_2D_3$ in different cell types, and variant VDR transcripts may play a role in tissue specific VDR actions in bone and calcium homeostasis.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Baker, A. R. et. al. (1988) Proc. Natl. Acad. Sci. USA 85, 3294-3298
2. Miyamoto, K. et. al. (1997) Mol. Endocrinol. 11, 1165-1179
3. Whitehead, R. H. et. al. (1987) Cancer Res. 47, 2683-2689
4. Slater, M. et al. (1994) Am. J. Physiology 267, E990-1001
5. Saijo, T. et. al. (1991) Amj. Hum. Genet. 49, 668-673
6. Lu, Z. et. al. (1997) Arch. Biochem. Biophys. 339, 99-106
7. Ebihara, K. et. al. (1996) Mol. Cell. Biol. 16, 3393-3400

The invention claimed is:

1. An isolated polypeptide comprising the amino acid sequence encoded by exon 1d of the human vitamin D receptor (VDR).

2. A polypeptide according to claim 1, wherein said polypeptide further comprises:

i) the amino acid sequence encoded by exon 1b of the human VDR; and/or ii) the amino acid sequence encoded by exon 1c of the human VDR.

3. A polypeptide according to claim 1, wherein the polypeptide comprises the amino acid seiuence encoded by exons 1d, 1c and 2-9 and consists essentially of a VDR isoform of approximately 477 amino acids.

4. A polypeptide according to claim 1, wherein the polypeptide comprises a sequence as shown in SEQ ID NO:9.

5. The polypeptide according to claim 2, wherein said polypeptide further comprises:

i) the amino acid sequence encoded by exon 1b of the human VDR; and ii) the amino acid sequence encoded by exon 1c of the human VDR.

6. The polypeptide according to claim 1, wherein said polypeptide further comprises the amino acid sequence encoded by exons 1d and 2-9 and consists essentially of VDR isoform of approximately 450 amino acids.

7. The polypeptide according to claim 1, wherein said polypeptide further comprises the amino acid sequence encoded by exons 1d and 2-9 and consists essentially of a truncated VDR isoform of approximately 72 amino acids.

8. The polypeptide according to claim 1, wherein the polypeptide comprises a sequence as shown in SEQ ID NO:10.

9. The polypeptide according to claim 1, wherein the polypeptide comprises a sequence as shown in SEQ ID NO:11.

* * * * *

UNITED STATES PATENT AND TRADEMARK OFFICE

CERTIFICATE OF CORRECTION

PATENT NO. : 7,317,078 B2
APPLICATION NO. : 11/156272
DATED : January 8, 2008
INVENTOR(S) : Linda Anne Crofts It is certified that error appears in the above-identified patent and that said Letters Patent is hereby corrected as shown below:

Col. 37 Claim 3 line 52: Delete “seiuence” and replace it with --sequence--.

Signed and Sealed this

First Day of July, 2008

Jon W. Dudas

JON W. DUDAS
*Director of the United States Patent and Trademark Office*

SEQUENCE LISTING

```
<160> NUMBER OF SEQ ID NOS: 28

<210> SEQ ID NO 1
<211> LENGTH: 96
```

-continued

<212> TYPE: DNA
<213> ORGANISM: Homo sapiens

<400> SEQUENCE: 1
gtttccttct tctgtcgggg cgccttggca tggagtggag gaataagaaa aggagcgatt 60
ggctgtcgat ggtgctcaga actgctggag tggagg 96

<210> SEQ ID NO 2
<211> LENGTH: 1463
<212> TYPE: DNA
<213> ORGANISM: Homo sapiens

<400> SEQUENCE: 2
gtttccttct tctgtcgggg cgccttggca tggagtggag gaataagaaa aggagcgatt 60
ggctgtcgat ggtgctcaga actgctggag tggaggaagc ctttgggtct gaagtgtctg 120
tgagacctca cagaagagca cccctgggct ccacttacct gccccctgct ccttcaggga 180
tggaggcaat ggcggccagc acttccctgc ctgaccctgg agactttgac cggaacgtgc 240
cccggatctg tggggtgtgt ggagaccgag ccactggctt tcacttcaat gctatgacct 300
gtgaaggctg caaaggcttc ttcaggcgaa gcatgaagcg gaaggcacta ttcacctgcc 360
ccttcaacgg ggactgccgc atcaccaagg acaaccgacg ccactgccag gcctgccggc 420
tcaaacgctg tgtggacatc ggcatgatga aggagttcat tctgacagat gaggaagtgc 480
agaggaagcg ggagatgatc ctgaagcgga aggaggagga ggccttgaag gacagtctgc 540
ggcccaagct gtctgaggag cagcagcgca tcattgccat actgctggac gcccaccata 600
agacctacga ccccacctac tccgacttct gccagttccg gcctccagtt cgtgtgaatg 660
atggtggagg gagccatcct tccaggccca actccagaca cactcccagc ttctctgggg 720
actcctcctc ctcctgctca gatcactgta tcacctcttc agacatgatg gactcgtcca 780
gcttctccaa tctggatctg agtgaagaag attcagatga cccttctgtg accctagagc 840
tgtcccagct ctccatgctg ccccacctgg ctgacctggt cagttacagc atccaaaagg 900
tcattggctt tgctaagatg ataccaggat tcagagacct cacctctgag gaccagatcg 960
tactgctgaa gtcaagtgcc attgaggtca tcatgttgcg ctccaatgag tccttcacca 1020
tggacgacat gtcctggacc tgtggcaacc aagactacaa gtaccgcgtc agtgacgtga 1080
ccaaagccgg acacagcctg gagctgattg agcccctcat caagttccag gtgggactga 1140
agaagctgaa cttgcatgag gaggagcatg tcctgctcat ggccatctgc atcgtctccc 1200
cagatcgtcc tggggtgcag gacgccgcgc tgattgaggc catccaggac cgcctgtcca 1260
acacactgca gacgtacatc cgctgccgcc acccgccccc gggcagccac ctgctctatg 1320
ccaagatgat ccagaagcta gccgacctgc gcagcctcaa tgaggagcac tccaagcagt 1380
accgctgcct ctccttccag cctgagtgca gcatgaagct aacgcccctt gtgctcgaag 1440
tgtttggcaa tgagatctcc tga 1463

<210> SEQ ID NO 3
<211> LENGTH: 1382
<212> TYPE: DNA
<213> ORGANISM: Homo sapiens

<400> SEQUENCE: 3
gtttccttct tctgtcgggg cgccttggca tggagtggag gaataagaaa aggagcgatt 60
ggctgtcgat ggtgctcaga actgctggag tggaggggat ggaggcaatg gcggccagca 120

-continued

```
cttccctgcc tgaccctgga gactttgacc ggaacgtgcc ccggatctgt ggggtgtgtg    180
gagaccgagc cactggcttt cacttcaatg ctatgacctg tgaaggctgc aaaggcttct    240
tcaggcgaag catgaagcgg aaggcactat tcacctgccc cttcaacggg gactgccgca    300
tcaccaagga caaccgacgc cactgccagg cctgccggct caaacgctgt gtggacatcg    360
gcatgatgaa ggagttcatt ctgacagatg aggaagtgca gaggaagcgg gagatgatcc    420
tgaagcggaa ggaggaggag gccttgaagg acagtctgcg gcccaagctg tctgaggagc    480
agcagcgcat cattgccata ctgctggacg cccaccataa gacctacgac cccacctact    540
ccgacttctg ccagttccgg cctccagttc gtgtgaatga tggtggaggg agccatcctt    600
ccaggcccaa ctccagacac actcccagct tctctgggga ctcctcctcc tcctgctcag    660
atcactgtat cacctcttca gacatgatgg actcgtccag cttctccaat ctggatctga    720
gtgaagaaga ttcagatgac ccttctgtga ccctagagct gtcccagctc tccatgctgc    780
cccacctggc tgacctggtc agttacagca tccaaaaggt cattggcttt gctaagatga    840
taccaggatt cagagacctc acctctgagg accagatcgt actgctgaag tcaagtgcca    900
ttgaggtcat catgttgcgc tccaatgagt ccttcaccat ggacgacatg tcctggacct    960
gtggcaacca agactacaag taccgcgtca gtgacgtgac caaagccgga cacagcctgg   1020
agctgattga gcccctcatc aagttccagg tgggactgaa gaagctgaac ttgcatgagg   1080
aggagcatgt cctgctcatg gccatctgca tcgtctcccc agatcgtcct ggggtgcagg   1140
acgccgcgct gattgaggcc atccaggacc gcctgtccaa cacactgcag acgtacatcc   1200
gctgccgcca cccgcccccg ggcagccacc tgctctatgc caagatgatc cagaagctag   1260
ccgacctgcg cagcctcaat gaggagcact ccaagcagta ccgctgcctc tccttccagc   1320
ctgagtgcag catgaagcta acgccccttg tgctcgaagt gtttggcaat gagatctcct   1380
ga                                                                  1382
```

<210> SEQ ID NO 4
<211> LENGTH: 1534
<212> TYPE: DNA
<213> ORGANISM: Homo sapiens

<400> SEQUENCE: 4

```
gtttccttct tctgtcgggg cgccttggca tggagtggag gaataagaaa aggagcgatt     60
ggctgtcgat ggtgctcaga actgctggag tggaggggat ggaggcaatg gcggccagca    120
cttccctgcc tgaccctgga gactttgacc ggaacgtgcc ccggatctgt ggggtgtgtg    180
gagaccgagc cactggcttt cacttcaatg ctatgacctg tgaaggctgc aaaggcttct    240
tcaggtgagc ccccctccca ggctctcccc agtggaaagg gagggagaag aagcaaggtg    300
tttccatgaa gggagccctt gcatttttca catctccttc cttacaatgt ccatggaaca    360
tgcggcgctc acagccacag gagcaggagg gtcttggcga agcatgaagc ggaaggcact    420
attcacctgc cccttcaacg gggactgccg catcaccaag gacaaccgac gccactgcca    480
ggcctgccgg ctcaaacgct gtgtggacat cggcatgatg aaggagttca ttctgacaga    540
tgaggaagtg cagaggaagc gggagatgat cctgaagcgg aaggaggagg aggccttgaa    600
ggacagtctg cggcccaagc tgtctgagga gcagcagcgc atcattgcca tactgctgga    660
cgcccaccat aagacctacg accccaccta ctccgacttc tgccagttcc ggcctccagt    720
tcgtgtgaat gatggtggag ggagccatcc ttccaggccc aactccagac acactcccag    780
cttctctggg gactcctcct cctcctgctc agatcactgt atcacctctt cagacatgat    840
```

```
ggactcgtcc agcttctcca atctggatct gagtgaagaa gattcagatg acccttctgt    900

gaccctagag ctgtcccagc tctccatgct gccccacctg gctgacctgg tcagttacag    960

catccaaaag gtcattggct ttgctaagat gataccagga ttcagagacc tcacctctga   1020

ggaccagatc gtactgctga agtcaagtgc cattgaggtc atcatgttgc gctccaatga   1080

gtccttcacc atggacgaca tgtcctggac ctgtggcaac caagactaca agtaccgcgt   1140

cagtgacgtg accaaagccg gacacagcct ggagctgatt gagcccctca tcaagttcca   1200

ggtgggactg aagaagctga acttgcatga ggaggagcat gtcctgctca tggccatctg   1260

catcgtctcc ccagatcgtc ctggggtgca ggacgccgcg ctgattgagg ccatccagga   1320

ccgcctgtcc aacacactgc agacgtacat ccgctgccgc cacccgcccc cgggcagcca   1380

cctgctctat gccaagatga tccagaagct agccgacctg cgcagcctca atgaggagca   1440

ctccaagcag taccgctgcc tctccttcca gcctgagtgc agcatgaagc taacgcccct   1500

tgtgctcgaa gtgtttggca atgagatctc ctga                               1534
```

```
<210> SEQ ID NO 5
<211> LENGTH: 207
<212> TYPE: DNA
<213> ORGANISM: Homo sapiens

<400> SEQUENCE: 5

tgcgaccttg gcggtgagcc tggggacagg ggtgaggcca gagacggacg gacgcagggg     60

cccggcccaa ggcgagggag aacagcggca ctaaggcaga aaggaagagg gcggtgtgtt    120

cacccgcagc ccaatccatc actcagcaac tcctagacgc tggtagaaag ttcctccgag    180

gagcctgcca tccagtcgtg cgtgcag                                        207
```

```
<210> SEQ ID NO 6
<211> LENGTH: 167
<212> TYPE: DNA
<213> ORGANISM: Homo sapiens

<400> SEQUENCE: 6

aggcagcatg aaacagtggg atgtgcagag agaagatctg ggtccagtag ctctgacact     60

cctcagctgt agaaaccttg acaactctgc acatcagttg tacaatggaa cggtattttt    120

tactcttcat gtctgaaaag gctatgataa agatcaagta agatatt                  167
```

```
<210> SEQ ID NO 7
<211> LENGTH: 1574
<212> TYPE: DNA
<213> ORGANISM: Homo sapiens

<400> SEQUENCE: 7

tgcgaccttg gcggtgagcc tggggacagg ggtgaggcca gagacggacg gacgcagggg     60

cccggcccaa ggcgagggag aacagcggca ctaaggcaga aaggaagagg gcggtgtgtt    120

cacccgcagc ccaatccatc actcagcaac tcctagacgc tggtagaaag ttcctccgag    180

gagcctgcca tccagtcgtg cgtgcagaag cctttgggtc tgaagtgtct gtgagacctc    240

acagaagagc acccctgggc tccacttacc tgccccctgc tccttcaggg atggaggcaa    300

tggcggccag cacttccctg cctgaccctg gagactttga ccggaacgtg ccccggatct    360

gtggggtgtg tggagaccga gccactggct ttcacttcaa tgctatgacc tgtgaaggct    420

gcaaaggctt cttcaggcga agcatgaagc ggaaggcact attcacctgc cccttcaacg    480
```

-continued

```
gggactgccg catcaccaag gacaaccgac gccactgcca ggcctgccgg ctcaaacgct    540

gtgtggacat cggcatgatg aaggagttca ttctgacaga tgaggaagtg cagaggaagc    600

gggagatgat cctgaagcgg aaggaggagg aggccttgaa ggacagtctg cggcccaagc    660

tgtctgagga gcagcagcgc atcattgcca tactgctgga cgcccaccat aagacctacg    720

accccaccta ctccgacttc tgccagttcc ggcctccagt tcgtgtgaat gatggtggag    780

ggagccatcc ttccaggccc aactccagac acactcccag cttctctggg gactcctcct    840

cctcctgctc agatcactgt atcacctctt cagacatgat ggactcgtcc agcttctcca    900

atctggatct gagtgaagaa gattcagatg acccttctgt gaccctagag ctgtcccagc    960

tctccatgct gccccacctg gctgacctgg tcagttacag catccaaaag gtcattggct   1020

ttgctaagat gataccagga ttcagagacc tcacctctga ggaccagatc gtactgctga   1080

agtcaagtgc cattgaggtc atcatgttgc gctccaatga gtccttcacc atggacgaca   1140

tgtcctggac ctgtggcaac caagactaca agtaccgcgt cagtgacgtg accaaagccg   1200

gacacagcct ggagctgatt gagcccctca tcaagttcca ggtgggactg aagaagctga   1260

acttgcatga ggaggagcat gtcctgctca tggccatctg catcgtctcc ccagatcgtc   1320

ctggggtgca ggacgccgcg ctgattgagg ccatccagga ccgcctgtcc aacacactgc   1380

agacgtacat ccgctgccgc cacccgcccc cgggcagcca cctgctctat gccaagatga   1440

tccagaagct agccgacctg cgcagcctca atgaggagca ctccaagcag taccgctgcc   1500

tctccttcca gcctgagtgc agcatgaagc taacgcccct tgtgctcgaa gtgtttggca   1560

atgagatctc ctga                                                      1574
```

<210> SEQ ID NO 8
<211> LENGTH: 122
<212> TYPE: DNA
<213> ORGANISM: Homo sapiens

<400> SEQUENCE: 8

```
ggctcctgaa cctagcccag ctggacggag aaatggactc tagcctcctc tgatagcctc     60

atgccaggcc ccgtgcacat tgctttgctt gcctccctca atcctcatag cttctctttg    120

gg                                                                   122
```

<210> SEQ ID NO 9
<211> LENGTH: 477
<212> TYPE: PRT
<213> ORGANISM: Homo sapiens

<400> SEQUENCE: 9

```
Met Glu Trp Arg Asn Lys Lys Arg Ser Asp Trp Leu Ser Met Val Leu
 1               5                  10                  15

Arg Thr Ala Gly Val Glu Glu Ala Phe Gly Ser Glu Val Ser Val Arg
            20                  25                  30

Pro His Arg Arg Ala Pro Leu Gly Ser Thr Tyr Leu Pro Pro Ala Pro
        35                  40                  45

Ser Gly Met Glu Ala Met Ala Ala Ser Thr Ser Leu Pro Asp Pro Gly
    50                  55                  60

Asp Phe Asp Arg Asn Val Pro Arg Ile Cys Gly Val Cys Gly Asp Arg
65                  70                  75                  80

Ala Thr Gly Phe His Phe Asn Ala Met Thr Cys Glu Gly Cys Lys Gly
                85                  90                  95

Phe Phe Arg Arg Ser Met Lys Arg Lys Ala Leu Phe Thr Cys Pro Phe
```

-continued

```
            100                 105                 110

Asn Gly Asp Cys Arg Ile Thr Lys Asp Asn Arg Arg His Cys Gln Ala
        115                 120                 125

Cys Arg Leu Lys Arg Cys Val Asp Ile Gly Met Met Lys Glu Phe Ile
    130                 135                 140

Leu Thr Asp Glu Glu Val Gln Arg Lys Arg Glu Met Ile Leu Lys Arg
145                 150                 155                 160

Lys Glu Glu Glu Ala Leu Lys Asp Ser Leu Arg Pro Lys Leu Ser Glu
                165                 170                 175

Glu Gln Gln Arg Ile Ile Ala Ile Leu Leu Asp Ala His His Lys Thr
            180                 185                 190

Tyr Asp Pro Thr Tyr Ser Asp Phe Cys Gln Phe Arg Pro Pro Val Arg
        195                 200                 205

Val Asn Asp Gly Gly Gly Ser His Pro Ser Arg Pro Asn Ser Arg His
    210                 215                 220

Thr Pro Ser Phe Ser Gly Asp Ser Ser Ser Ser Cys Ser Asp His Cys
225                 230                 235                 240

Ile Thr Ser Ser Asp Met Met Asp Ser Ser Ser Phe Ser Asn Leu Asp
                245                 250                 255

Leu Ser Glu Glu Asp Ser Asp Asp Pro Ser Val Thr Leu Glu Leu Ser
            260                 265                 270

Gln Leu Ser Met Leu Pro His Leu Ala Asp Leu Val Ser Tyr Ser Ile
        275                 280                 285

Gln Lys Val Ile Gly Phe Ala Lys Met Ile Pro Gly Phe Arg Asp Leu
    290                 295                 300

Thr Ser Glu Asp Gln Ile Val Leu Leu Lys Ser Ser Ala Ile Glu Val
305                 310                 315                 320

Ile Met Leu Arg Ser Asn Glu Ser Phe Thr Met Asp Asp Met Ser Trp
                325                 330                 335

Thr Cys Gly Asn Gln Asp Tyr Lys Tyr Arg Val Ser Asp Val Thr Lys
            340                 345                 350

Ala Gly His Ser Leu Glu Leu Ile Glu Pro Leu Ile Lys Phe Gln Val
        355                 360                 365

Gly Leu Lys Lys Leu Asn Leu His Glu Glu Glu His Val Leu Leu Met
    370                 375                 380

Ala Ile Cys Ile Val Ser Pro Asp Arg Pro Gly Val Gln Asp Ala Ala
385                 390                 395                 400

Leu Ile Glu Ala Ile Gln Asp Arg Leu Ser Asn Thr Leu Gln Thr Tyr
                405                 410                 415

Ile Arg Cys Arg His Pro Pro Pro Gly Ser His Leu Leu Tyr Ala Lys
            420                 425                 430

Met Ile Gln Lys Leu Ala Asp Leu Arg Ser Leu Asn Glu Glu His Ser
        435                 440                 445

Lys Gln Tyr Arg Cys Leu Ser Phe Gln Pro Glu Cys Ser Met Lys Leu
    450                 455                 460

Thr Pro Leu Val Leu Glu Val Phe Gly Asn Glu Ile Ser
465                 470                 475
```

<210> SEQ ID NO 10
<211> LENGTH: 450
<212> TYPE: PRT
<213> ORGANISM: Homo sapiens

<400> SEQUENCE: 10

-continued

```
Met Glu Trp Arg Asn Lys Lys Arg Ser Asp Trp Leu Ser Met Val Leu
 1               5                  10                  15

Arg Thr Ala Gly Val Glu Gly Met Glu Ala Met Ala Ala Ser Thr Ser
            20                  25                  30

Leu Pro Asp Pro Gly Asp Phe Asp Arg Asn Val Pro Arg Ile Cys Gly
        35                  40                  45

Val Cys Gly Asp Arg Ala Thr Gly Phe His Phe Asn Ala Met Thr Cys
    50                  55                  60

Glu Gly Cys Lys Gly Phe Phe Arg Arg Ser Met Lys Arg Lys Ala Leu
65                  70                  75                  80

Phe Thr Cys Pro Phe Asn Gly Asp Cys Arg Ile Thr Lys Asp Asn Arg
                85                  90                  95

Arg His Cys Gln Ala Cys Arg Leu Lys Arg Cys Val Asp Ile Gly Met
            100                 105                 110

Met Lys Glu Phe Ile Leu Thr Asp Glu Glu Val Gln Arg Lys Arg Glu
        115                 120                 125

Met Ile Leu Lys Arg Lys Glu Glu Glu Ala Leu Lys Asp Ser Leu Arg
    130                 135                 140

Pro Lys Leu Ser Glu Glu Gln Gln Arg Ile Ile Ala Ile Leu Leu Asp
145                 150                 155                 160

Ala His His Lys Thr Tyr Asp Pro Thr Tyr Ser Asp Phe Cys Gln Phe
                165                 170                 175

Arg Pro Pro Val Arg Val Asn Asp Gly Gly Gly Ser His Pro Ser Arg
            180                 185                 190

Pro Asn Ser Arg His Thr Pro Ser Phe Ser Gly Asp Ser Ser Ser Ser
        195                 200                 205

Cys Ser Asp His Cys Ile Thr Ser Ser Asp Met Met Asp Ser Ser Ser
    210                 215                 220

Phe Ser Asn Leu Asp Leu Ser Glu Glu Asp Ser Asp Asp Pro Ser Val
225                 230                 235                 240

Thr Leu Glu Leu Ser Gln Leu Ser Met Leu Pro His Leu Ala Asp Leu
                245                 250                 255

Val Ser Tyr Ser Ile Gln Lys Val Ile Gly Phe Ala Lys Met Ile Pro
            260                 265                 270

Gly Phe Arg Asp Leu Thr Ser Glu Asp Gln Ile Val Leu Leu Lys Ser
        275                 280                 285

Ser Ala Ile Glu Val Ile Met Leu Arg Ser Asn Glu Ser Phe Thr Met
    290                 295                 300

Asp Asp Met Ser Trp Thr Cys Gly Asn Gln Asp Tyr Lys Tyr Arg Val
305                 310                 315                 320

Ser Asp Val Thr Lys Ala Gly His Ser Leu Glu Leu Ile Glu Pro Leu
                325                 330                 335

Ile Lys Phe Gln Val Gly Leu Lys Lys Leu Asn Leu His Glu Glu Glu
            340                 345                 350

His Val Leu Leu Met Ala Ile Cys Ile Val Ser Pro Asp Arg Pro Gly
        355                 360                 365

Val Gln Asp Ala Ala Leu Ile Glu Ala Ile Gln Asp Arg Leu Ser Asn
    370                 375                 380

Thr Leu Gln Thr Tyr Ile Arg Cys Arg His Pro Pro Pro Gly Ser His
385                 390                 395                 400

Leu Leu Tyr Ala Lys Met Ile Gln Lys Leu Ala Asp Leu Arg Ser Leu
                405                 410                 415

Asn Glu Glu His Ser Lys Gln Tyr Arg Cys Leu Ser Phe Gln Pro Glu
```

-continued

```
            420                 425                 430

Cys Ser Met Lys Leu Thr Pro Leu Val Leu Glu Val Phe Gly Asn Glu
        435                 440                 445

Ile Ser
    450


<210> SEQ ID NO 11
<211> LENGTH: 72
<212> TYPE: PRT
<213> ORGANISM: Homo sapiens

<400> SEQUENCE: 11

Met Glu Trp Arg Asn Lys Lys Arg Ser Asp Trp Leu Ser Met Val Leu
 1               5                  10                  15

Arg Thr Ala Gly Val Glu Gly Met Glu Ala Met Ala Ala Ser Thr Ser
            20                  25                  30

Leu Pro Asp Pro Gly Asp Phe Asp Arg Asn Val Pro Arg Ile Cys Gly
        35                  40                  45

Val Cys Gly Asp Arg Ala Thr Gly Phe His Phe Asn Ala Met Thr Cys
    50                  55                  60

Glu Gly Cys Lys Gly Phe Phe Arg
65                  70


<210> SEQ ID NO 12
<211> LENGTH: 427
<212> TYPE: PRT
<213> ORGANISM: Homo sapiens

<400> SEQUENCE: 12

Met Glu Ala Met Ala Ala Ser Thr Ser Leu Pro Asp Pro Gly Asp Phe
 1               5                  10                  15

Asp Arg Asn Val Pro Arg Ile Cys Gly Val Cys Gly Asp Arg Ala Thr
            20                  25                  30

Gly Phe His Phe Asn Ala Met Thr Cys Glu Gly Cys Lys Gly Phe Phe
        35                  40                  45

Arg Arg Ser Met Lys Arg Lys Ala Leu Phe Thr Cys Pro Phe Asn Gly
    50                  55                  60

Asp Cys Arg Ile Thr Lys Asp Asn Arg Arg His Cys Gln Ala Cys Arg
65                  70                  75                  80

Leu Lys Arg Cys Val Asp Ile Gly Met Met Lys Glu Phe Ile Leu Thr
                85                  90                  95

Asp Glu Glu Val Gln Arg Lys Arg Glu Met Ile Leu Lys Arg Lys Glu
            100                 105                 110

Glu Glu Ala Leu Lys Asp Ser Leu Arg Pro Lys Leu Ser Glu Glu Gln
        115                 120                 125

Gln Arg Ile Ile Ala Ile Leu Leu Asp Ala His His Lys Thr Tyr Asp
    130                 135                 140

Pro Thr Tyr Ser Asp Phe Cys Gln Phe Arg Pro Pro Val Arg Val Asn
145                 150                 155                 160

Asp Gly Gly Gly Ser His Pro Ser Arg Pro Asn Ser Arg His Thr Pro
                165                 170                 175

Ser Phe Ser Gly Asp Ser Ser Ser Ser Cys Ser Asp His Cys Ile Thr
            180                 185                 190

Ser Ser Asp Met Met Asp Ser Ser Ser Phe Ser Asn Leu Asp Leu Ser
        195                 200                 205

Glu Glu Asp Ser Asp Asp Pro Ser Val Thr Leu Glu Leu Ser Gln Leu
```

-continued

```
    210                 215                 220

Ser Met Leu Pro His Leu Ala Asp Leu Val Ser Tyr Ser Ile Gln Lys
225                 230                 235                 240

Val Ile Gly Phe Ala Lys Met Ile Pro Gly Phe Arg Asp Leu Thr Ser
                245                 250                 255

Glu Asp Gln Ile Val Leu Leu Lys Ser Ser Ala Ile Glu Val Ile Met
            260                 265                 270

Leu Arg Ser Asn Glu Ser Phe Thr Met Asp Asp Met Ser Trp Thr Cys
        275                 280                 285

Gly Asn Gln Asp Tyr Lys Tyr Arg Val Ser Asp Val Thr Lys Ala Gly
    290                 295                 300

His Ser Leu Glu Leu Ile Glu Pro Leu Ile Lys Phe Gln Val Gly Leu
305                 310                 315                 320

Lys Lys Leu Asn Leu His Glu Glu Glu His Val Leu Leu Met Ala Ile
                325                 330                 335

Cys Ile Val Ser Pro Asp Arg Pro Gly Val Gln Asp Ala Ala Leu Ile
            340                 345                 350

Glu Ala Ile Gln Asp Arg Leu Ser Asn Thr Leu Gln Thr Tyr Ile Arg
        355                 360                 365

Cys Arg His Pro Pro Pro Gly Ser His Leu Leu Tyr Ala Lys Met Ile
    370                 375                 380

Gln Lys Leu Ala Asp Leu Arg Ser Leu Asn Glu Glu His Ser Lys Gln
385                 390                 395                 400

Tyr Arg Cys Leu Ser Phe Gln Pro Glu Cys Ser Met Lys Leu Thr Pro
                405                 410                 415

Leu Val Leu Glu Val Phe Gly Asn Glu Ile Ser
            420                 425
```

<210> SEQ ID NO 13
<211> LENGTH: 142
<212> TYPE: DNA
<213> ORGANISM: Homo sapiens

<400> SEQUENCE: 13

```
atcccttaag ggctcctgaa cctagcccag ctggacggag aaatggactc tagcctcctc      60

tgatagcctc atgccaggcc ccgtgcacat tgctttgctt gcctccctca atcctcatag     120

ctcctctttg gggtaagtac ag                                              142
```

<210> SEQ ID NO 14
<211> LENGTH: 26
<212> TYPE: PRT
<213> ORGANISM: Homo sapiens

<400> SEQUENCE: 14

```
Met Glu Ala Met Ala Ala Ser Thr Ser Leu Pro Asp Pro Gly Asp Phe
 1               5                  10                  15

Asp Arg Asn Val Pro Arg Ile Asp Asx Asp
            20                  25
```

<210> SEQ ID NO 15
<211> LENGTH: 76
<212> TYPE: PRT
<213> ORGANISM: Homo sapiens

<400> SEQUENCE: 15

```
Met Glu Trp Arg Asn Lys Lys Arg Ser Asp Trp Leu Ser Met Val Leu
 1               5                  10                  15
```

-continued

```
Arg Thr Ala Gly Val Glu Glu Ala Phe Gly Ser Glu Val Ser Val Arg
            20                  25                  30

Pro His Arg Arg Ala Pro Leu Gly Ser Thr Tyr Leu Pro Pro Ala Pro
        35                  40                  45

Ser Gly Met Glu Ala Met Ala Ala Ser Thr Ser Leu Pro Asp Pro Gly
    50                  55                  60

Asp Phe Asp Arg Asn Val Pro Arg Ile Asp Asx Asp
65                  70                  75


<210> SEQ ID NO 16
<211> LENGTH: 49
<212> TYPE: PRT
<213> ORGANISM: Homo sapiens

<400> SEQUENCE: 16

Met Glu Trp Arg Asn Lys Lys Arg Ser Asp Trp Leu Ser Met Val Leu
 1               5                  10                  15

Arg Thr Ala Gly Val Glu Gly Met Glu Ala Met Ala Ala Ser Thr Ser
            20                  25                  30

Leu Pro Asp Pro Gly Asp Phe Asp Arg Asn Val Pro Arg Ile Asp Asx
        35                  40                  45

Asp


<210> SEQ ID NO 17
<211> LENGTH: 1463
<212> TYPE: DNA
<213> ORGANISM: Homo sapiens

<400> SEQUENCE: 17

caaaggaaga agacagcccc gcggaaccgt acctcacctc cttattcttt tcctcgctaa      60

ccgacagcta ccacgagtct tgacgacctc acctccttcg ctttgggtct gaagtgtctg     120

tgagacctca cagaagagca cccctgggct ggtgaatgga cgggggacga ggaagtccct     180

acctccgtta ccgccggtcg tgaagggacg gactgggacc tctgaaactg gccttgcacg     240

gggcctagac accccacaca cctctggctc ggtgaccgaa agtgaagtta cgatactgga     300

cacttccgac gtttccgaag aagtccgctt cgtacttcgc cttccgtgat aagtggacgg     360

ggaagttgcc cctgacggcg tagtggttcc tgttggctgc ggtgacggtc cggacggccg     420

agtttgcgac acacctgtag ccgtactact tcctcaagta agactgtcta ctccttcacg     480

tctccttcgc cctctactag gacttcgcct tcctcctcct ccggaacttc ctgtcagacg     540

ccgggttcga cagactcctc gtcgtcgcgt agtaacggta tgacgacctg cgggtggtat     600

tctggatgct ggggtggatg aggctgaaga cggtcaaggc cggaggtcaa gcacacttac     660

taccacctcc ctcggtagga aggtccgggt tgaggtctgt gtgagggtcg aagagacccc     720

tgaggaggag gaggacgagt ctagtgacat agtggagaag tctgtactac ctgagcaggt     780

cgaagaggtt agacctagac tcacttcttc taagtctact gggaagacac tgggatctcg     840

acagggtcga gaggtacgac ggggtggacc gactggacca gtcaatgtcg taggttttcc     900

agtaaccgaa acgattctac tatggtccta agtctctgga gtggagactc ctggtctagc     960

atgacgactt cagttcacgg taactccagt agtacaacgc gaggttactc aggaagtggt    1020

acctgctgta caggacctgg acaccgttgg ttctgatgtt catggcgcag tcactgcact    1080

ggtttcggcc tgtgtcggac ctcgactaac tcggggagta gttcaaggtc caccctgact    1140

tcttcgactt gaacgtactc ctcctcgtac aggacgagta ccggtagacg tagcagaggg    1200
```

-continued

```
gtctagcagg accccacgtc ctgcggcgcg actaactccg gtaggtcctg gcggacaggt   1260

tgtgtgacgt ctgcatgtag gcgacggcgg tgggcggggg cccgtcggtg gacgagatac   1320

ggttctacta ggtcttcgat cggctggacg cgtcggagtt actcctcgtg aggttcgtca   1380

tggcgacgga gaggaaggtc ggactcacgt cgtacttcga ttgcggggaa cacgagcttc   1440

acaaaccgtt actctagagg act                                           1463
```

<210> SEQ ID NO 18
<211> LENGTH: 1382
<212> TYPE: DNA
<213> ORGANISM: Homo sapiens

<400> SEQUENCE: 18

```
caaaggaaga agacagcccc gcggaaccgt acctcacctc cttattcttt tcctcgctaa     60

ccgacagcta ccacgagtct tgacgacctc acctccccta cctccgttac cgccggtcgt    120

gaagggacgg actgggacct ctgaaactgg ccttgcacgg ggcctagaca ccccacacac    180

ctctggctcg gtgaccgaaa gtgaagttac gatactggac acttccgacg tttccgaaga    240

agtccgcttc gtacttcgcc ttccgtgata agtggacggg gaagttgccc ctgacggcgt    300

agtggttcct gttggctgcg gtgacggtcc ggacggccga gtttgcgaca cacctgtagc    360

cgtactactt cctcaagtaa gactgtctac tccttcacgt ctccttcgcc ctctactagg    420

acttcgcctt cctcctcctc cggaacttcc tgtcagacgc cgggttcgac agactcctcg    480

tcgtcgcgta gtaacggtat gacgacctgc gggtggtatt ctggatgctg gggtggatga    540

ggctgaagac ggtcaaggcc ggaggtcaag cacacttact accacctccc tcggtaggaa    600

ggtccgggtt gaggtctgtg tgagggtcga agagacccct gaggaggagg aggacgagtc    660

tagtgacata gtggagaagt ctgtactacc tgagcaggtc gaagaggtta gacctagact    720

cacttcttct aagtctactg ggaagacact gggatctcga cagggtcgag aggtacgacg    780

gggtggaccg actggaccag tcaatgtcgt aggttttcca gtaaccgaaa cgattctact    840

atggtcctaa gtctctggag tggagactcc tggtctagca tgacgacttc agttcacggt    900

aactccagta gtacaacgcg aggttactca ggaagtggta cctgctgtac aggacctgga    960

caccgttggt tctgatgttc atggcgcagt cactgcactg gtttcggcct gtgtcggacc   1020

tcgactaact cggggagtag ttcaaggtcc accctgactt cttcgacttg aacgtactcc   1080

tcctcgtaca ggacgagtac cggtagacgt agcagagggg tctagcagga ccccacgtcc   1140

tgcggcgcga ctaactccgg taggtcctgg cggacaggtt gtgtgacgtc tgcatgtagg   1200

cgacggcggt gggcgggggc ccgtcggtgg acgagatacg gttctactag gtcttcgatc   1260

ggctggacgc gtcggagtta ctcctcgtga ggttcgtcat ggcgacggag aggaaggtcg   1320

gactcacgtc gtacttcgat tgcggggaac acgagcttca caaaccgtta ctctagagga   1380

ct                                                                  1382
```

<210> SEQ ID NO 19
<211> LENGTH: 1534
<212> TYPE: DNA
<213> ORGANISM: Homo sapiens

<400> SEQUENCE: 19

```
caaaggaaga agacagcccc gcggaaccgt acctcacctc cttattcttt tcctcgctaa     60

ccgacagcta ccacgagtct tgacgacctc acctccccta cctccgttac cgccggtcgt    120
```

-continued

```
gaagggacgg actgggacct ctgaaactgg ccttgcacgg ggcctagaca ccccacacac    180
ctctggctcg gtgaccgaaa gtgaagttac gatactggac acttccgacg tttccgaaga    240
agtccactcg gggggagggt ccgagagggg tcacctttcc ctccctcttc ttcgttccac    300
aaaggtactt ccctcgggaa cgtaaaaagt gtagaggaag gaatgttaca ggtaccttgt    360
acgccgcgag tgtcggtgtc ctcgtcctcc cagaaccgct tcgtacttcg ccttccgtga    420
taagtggacg gggaagttgc ccctgacggc gtagtggttc ctgttggctg cggtgacggt    480
ccggacggcc gagtttgcga cacacctgta gccgtactac ttcctcaagt aagactgtct    540
actccttcac gtctccttcg ccctctacta ggacttcgcc ttcctcctcc tccggaactt    600
cctgtcagac gccgggttcg acagactcct cgtcgtcgcg tagtaacggt atgacgacct    660
gcgggtggta ttctggatgc tggggtggat gaggctgaag acggtcaagg ccggaggtca    720
agcacactta ctaccacctc cctcggtagg aaggtccggg ttgaggtctg tgtgagggtc    780
gaagagaccc ctgaggagga ggaggacgag tctagtgaca tagtggagaa gtctgtacta    840
cctgagcagg tcgaagaggt tagacctaga ctcacttctt ctaagtctac tgggaagaca    900
ctgggatctc gacagggtcg agaggtacga cggggtggac cgactggacc agtcaatgtc    960
gtaggttttc cagtaaccga aacgattcta ctatggtcct aagtctctgg agtggagact   1020
cctggtctag catgacgact tcagttcacg gtaactccag tagtacaacg cgaggttact   1080
caggaagtgg tacctgctgt acaggacctg gacaccgttg gttctgatgt tcatggcgca   1140
gtcactgcac tggtttcggc ctgtgtcgga cctcgactaa ctcggggagt agttcaaggt   1200
ccaccctgac ttcttcgact tgaacgtact cctcctcgta caggacgagt accggtagac   1260
gtagcagagg ggtctagcag gaccccacgt cctgcggcgc gactaactcc ggtaggtcct   1320
ggcggacagg ttgtgtgacg tctgcatgta ggcgacggcg gtgggcgggg gcccgtcggt   1380
ggacgagata cggttctact aggtcttcga tcggctggac gcgtcggagt tactcctcgt   1440
gaggttcgtc atggcgacgg agaggaaggt cggactcacg tcgtacttcg attgcgggga   1500
acacgagctt cacaaaccgt tactctagag gact                               1534
```

<210> SEQ ID NO 20
<211> LENGTH: 1574
<212> TYPE: DNA
<213> ORGANISM: Homo sapiens

<400> SEQUENCE: 20

```
acgctggaac cgccactcgg acccctgtcc ccactccggt ctctgcctgc ctgcgtcccc     60
gggccgggtt ccgctccctc ttgtcgccgt gattccgtct ttccttctcc cgccacacaa    120
gtgggcgtcg ggttaggtag tgagtcgttg aggatctgcg accatctttc aaggaggctc    180
ctcggacggt aggtcagcac gcacgtcttc ggaaacccag acttcacaga cactctggag    240
tgtcttctcg tggggacccg aggtgaatgg acgggggacg aggaagtccc tacctccgtt    300
accgccggtc gtgaagggac ggactgggac ctctgaaact ggccttgcac ggggcctaga    360
caccccacac acctctggct cggtgaccga aagtgaagtt acgatactgg acacttccga    420
cgtttccgaa gaagtccgct tcgtacttcg ccttccgtga taagtggacg gggaagttgc    480
ccctgacggc gtagtggttc ctgttggctg cggtgacggt ccggacggcc gagtttgcga    540
cacacctgta gccgtactac ttcctcaagt aagactgtct actccttcac gtctccttcg    600
ccctctacta ggacttcgcc ttcctcctcc tccggaactt cctgtcagac gccgggttcg    660
acagactcct cgtcgtcgcg tagtaacggt atgacgacct gcgggtggta ttctggatgc    720
```

-continued

```
tggggtggat gaggctgaag acggtcaagg ccggaggtca agcacactta ctaccacctc    780

cctcggtagg aaggtccggg ttgaggtctg tgtgagggtc gaagagaccc ctgaggagga    840

ggaggacgag tctagtgaca tagtggagaa gtctgtacta cctgagcagg tcgaagaggt    900

tagacctaga ctcacttctt ctaagtctac tgggaagaca ctgggatctc gacagggtcg    960

agaggtacga cggggtggac cgactggacc agtcaatgtc gtaggttttc cagtaaccga   1020

aacgattcta ctatggtcct aagtctctgg agtggagact cctggtctag catgacgact   1080

tcagttcacg gtaactccag tagtacaacg cgaggttact caggaagtgg tacctgctgt   1140

acaggacctg gacaccgttg gttctgatgt tcatggcgca gtcactgcac tggtttcggc   1200

ctgtgtcgga cctcgactaa ctcggggagt agttcaaggt ccaccctgac ttcttcgact   1260

tgaacgtact cctcctcgta caggacgagt accggtagac gtagcagagg ggtctagcag   1320

gaccccacgt cctgcggcgc gactaactcc ggtaggtcct ggcggacagg ttgtgtgacg   1380

tctgcatgta ggcgacggcg gtgggcgggg gcccgtcggt ggacgagata cggttctact   1440

aggtcttcga tcggctggac gcgtcggagt tactcctcgt gaggttcgtc atggcgacgg   1500

agaggaaggt cggactcacg tcgtacttcg attgcgggga acacgagctt cacaaaccgt   1560

tactctagag gact                                                     1574
```

<210> SEQ ID NO 21
<211> LENGTH: 22
<212> TYPE: PRT
<213> ORGANISM: Homo sapiens

<400> SEQUENCE: 21

```
Met Glu Trp Arg Asn Lys Lys Arg Ser Asp Trp Leu Ser Met Val Leu
 1               5                  10                  15

Arg Thr Ala Gly Val Glu
            20
```

<210> SEQ ID NO 22
<211> LENGTH: 106
<212> TYPE: DNA
<213> ORGANISM: Homo sapiens

<400> SEQUENCE: 22

```
gtttccttct tctgtcgggg cgccttggca tggagtggag gaataagaaa aggagcgatt     60

ggctgtcgat ggtgctcaga actgctggag tggagggtgt gtaacc                  106
```

<210> SEQ ID NO 23
<211> LENGTH: 27
<212> TYPE: DNA
<213> ORGANISM: Homo sapiens

<400> SEQUENCE: 23

```
ccgcttcatg cttcgcctga agaagcc                                        27
```

<210> SEQ ID NO 24
<211> LENGTH: 29
<212> TYPE: DNA
<213> ORGANISM: Homo Sapiens

<400> SEQUENCE: 24

```
tgcagaattc acaggtcata gcattgaag                                      29
```

<210> SEQ ID NO 25

-continued

```
<211> LENGTH: 22
<212> TYPE: DNA
<213> ORGANISM: Homo sapiens

<400> SEQUENCE: 25

ggctgtcgat ggtgctcaga ac                                              22


<210> SEQ ID NO 26
<211> LENGTH: 22
<212> TYPE: DNA
<213> ORGANISM: Homo sapiens

<400> SEQUENCE: 26

aagttcctcc gaggagcctg cc                                              22


<210> SEQ ID NO 27
<211> LENGTH: 5
<212> TYPE: PRT
<213> ORGANISM: Homo sapiens

<400> SEQUENCE: 27

Arg Asn Lys Lys Arg
 1               5


<210> SEQ ID NO 28
<211> LENGTH: 5
<212> TYPE: PRT
<213> ORGANISM: Homo sapiens

<400> SEQUENCE: 28

Arg Pro His Arg Arg
 1               5
```